United States Patent
James et al.

(10) Patent No.: US 6,647,446 B1
(45) Date of Patent: Nov. 11, 2003

(54) METHOD AND SYSTEM FOR USING A NEW BUS IDENTIFIER RESULTING FROM A BUS TOPOLOGY CHANGE

(75) Inventors: David V. James, Palo Alto, CA (US); Bruce Fairman, Woodside, CA (US); David Hunter, Santa Barbara, CA (US); Hisato Shima, Mountain View, CA (US)

(73) Assignees: Sony Corporation, Tokyo (JP); Sony Electronics Inc., Park Ridge, NJ (US)

( * ) Notice: Subject to any disclaimer, the term of this patent is extended or adjusted under 35 U.S.C. 154(b) by 0 days.

(21) Appl. No.: 09/531,061

(22) Filed: Mar. 18, 2000

Related U.S. Application Data

(60) Provisional application No. 60/125,351, filed on Mar. 19, 1999.

(51) Int. Cl.$^7$ .................. G06F 15/173; G06F 13/00; G06F 13/40
(52) U.S. Cl. .................. 710/100; 710/103; 710/126; 709/221; 709/224; 709/227; 709/228; 709/242; 709/245; 709/253; 713/100; 714/3; 714/7
(58) Field of Search ................ 709/220–224, 709/227, 228, 242, 245, 253; 710/8–10, 62, 63, 100, 101–104, 126; 713/1, 100; 714/3, 7

(56) References Cited

U.S. PATENT DOCUMENTS

| | | | |
|---|---|---|---|
| 4,538,259 A | 8/1985 | Moore ..................... 370/60 |
| 4,935,894 A | 6/1990 | Ternes ..................... 364/900 |
| 5,381,138 A | 1/1995 | Stair et al. ............. 340/825.44 |
| 5,402,416 A | 3/1995 | Cieslak et al. ............. 370/60 |
| 5,485,505 A | 1/1996 | Norman et al. ............. 379/58 |
| 5,511,165 A | 4/1996 | Brady et al. ............ 395/200.01 |
| 5,574,869 A | * 11/1996 | Young et al. ............. 710/126 |
| 5,603,084 A | 2/1997 | Henry, Jr. et al. ........ 455/33.1 |
| 5,623,483 A | 4/1997 | Agrawal et al. ............ 370/253 |
| 5,675,794 A | * 10/1997 | Meredith ..................... 713/1 |
| 5,684,796 A | 11/1997 | Abidi et al. ............... 370/389 |
| 5,684,959 A | 11/1997 | Bhat et al. |
| 5,689,499 A | 11/1997 | Hullett et al. .............. 370/235 |
| 5,717,853 A | 2/1998 | Deshpande et al. |
| 5,724,517 A | * 3/1998 | Cook et al. ................ 709/227 |
| 5,734,824 A | 3/1998 | Choi ..................... 395/200.11 |
| 5,751,967 A | 5/1998 | Raab et al. ............ 395/200.58 |
| 5,757,772 A | 5/1998 | Thornberg et al. ......... 370/236 |
| 5,764,930 A | 6/1998 | Staats ...................... 395/287 |
| 5,774,683 A | 6/1998 | Gulick ..................... 395/309 |
| 5,790,530 A | 8/1998 | Moh et al. ................. 370/363 |
| 5,790,815 A | 8/1998 | Swanstrom et al. ....... 395/309 |
| 5,812,774 A | 9/1998 | Kempf et al. .......... 395/200.42 |
| 5,825,752 A | 10/1998 | Fujimori et al. ............ 370/260 |
| 5,832,245 A | 11/1998 | Gulick ..................... 395/309 |
| 5,842,124 A | 11/1998 | Kenagy et al. ............ 455/418 |
| 5,848,266 A | 12/1998 | Scheurich ................. 395/558 |

(List continued on next page.)

FOREIGN PATENT DOCUMENTS

| WO | WO 00/57263 | * 9/2000 | ............. G06F/3/00 |

OTHER PUBLICATIONS

1394 Trade Association, The Multimedia Connection, TA Document–1999025, AV/C General–Descriptor and Info Block Mechanism, Draft 0.2 :212, Dec. 17, 1999.

(List continued on next page.)

*Primary Examiner*—Jeffrey Gaffin
*Assistant Examiner*—Tanh Nguyen
(74) *Attorney, Agent, or Firm*—Blakely, Sokoloff, Taylor & Zafman LLP

(57) ABSTRACT

A method and system for using a new bus identifier in an interconnect, and the interconnect including a plurality of nodes and at least one bus bridge. A configuration change is determined on the first bus connected to the plurality of nodes. Each node has a corresponding bus identifier. A new bus identifier is assigned for each node having a changed state if a configuration change is determined on the first bus.

33 Claims, 19 Drawing Sheets

U.S. PATENT DOCUMENTS

| | | | |
|---|---|---|---|
| 5,854,910 A | 12/1998 | Gulick | 395/309 |
| 5,870,387 A | 2/1999 | Mulla | 370/258 |
| 5,872,524 A | 2/1999 | Iida | 340/825.52 |
| 5,872,944 A | 2/1999 | Goldrian et al. | 395/306 |
| 5,875,301 A | 2/1999 | Duckwall et al. | 395/200.51 |
| 5,883,621 A * | 3/1999 | Iwamura | 345/719 |
| 5,892,929 A | 4/1999 | Welker | 395/287 |
| 5,901,332 A | 5/1999 | Gephardt et al. | 395/861 |
| 5,905,732 A | 5/1999 | Fimoff et al. | 370/516 |
| 5,910,178 A | 6/1999 | Moh et al. | 709/232 |
| 5,920,267 A | 7/1999 | Tattersall et al. | 340/825.05 |
| 5,923,673 A | 7/1999 | Henrikson | 371/20.1 |
| 5,930,703 A | 7/1999 | Cairns | 455/418 |
| 5,935,208 A | 8/1999 | Duckwall et al. | 709/221 |
| 5,941,964 A | 8/1999 | Young et al. | 710/100 |
| 5,961,623 A | 10/1999 | James et al. | 710/113 |
| 5,970,234 A | 10/1999 | Jin | 395/291 |
| 5,974,036 A | 10/1999 | Acharya et al. | 370/331 |
| 5,978,854 A | 11/1999 | Fujimori et al. | 709/245 |
| 5,991,520 A | 11/1999 | Smyers et al. | 395/280 |
| 6,005,852 A | 12/1999 | Kokko et al. | 370/329 |
| 6,023,732 A | 2/2000 | Moh et al. | 709/232 |
| 6,032,211 A | 2/2000 | Hewitt | 710/107 |
| 6,038,625 A * | 3/2000 | Ogino et al. | 709/328 |
| 6,055,561 A | 4/2000 | Feldman et al. | 709/200 |
| 6,072,772 A | 6/2000 | Charny et al. | 370/229 |
| 6,085,270 A | 7/2000 | Gulick | 710/100 |
| 6,104,706 A | 8/2000 | Richter et al. | 370/263 |
| 6,108,718 A | 8/2000 | Fujimori et al. | 710/9 |
| 6,119,243 A | 9/2000 | Garney et al. | 713/600 |
| 6,131,119 A | 10/2000 | Fukui | 709/224 |
| 6,137,777 A | 10/2000 | Vaid et al. | 370/230 |
| 6,138,178 A | 10/2000 | Watanabe | 710/8 |
| 6,138,196 A | 10/2000 | Takayama et al. | 710/105 |
| 6,141,767 A | 10/2000 | Hu et al. | 714/1 |
| 6,151,651 A | 11/2000 | Hewitt et al. | 710/129 |
| 6,167,477 A * | 12/2000 | Garnett et al. | 710/129 |
| 6,185,632 B1 | 2/2001 | Berkema | 710/20 |
| 6,192,428 B1 | 2/2001 | Abramson et al. | 710/52 |
| 6,366,964 B1 * | 4/2002 | Shima et al. | 710/8 |
| 6,374,316 B1 * | 4/2002 | James et al. | 710/104 |
| 6,389,496 B1 * | 5/2002 | Matsuda | 710/131 |
| 6,519,671 B1 * | 2/2003 | Kondou et al. | 710/311 |

OTHER PUBLICATIONS

1394 Trade Association, The Multimedia Connection, TA Document 1999026, AV/C General Command and Response Model 4.0, Draft 0.1:35, May 22, 1999, pp. 1–46.

Gary Hoffman, Daniel Moore, "IEEE 1394: A Ubiquitous Bus", Compcon '95, Mar. 5–9, 1995, 9 pages.

Roger Jennings, "Fire on the Wire: The IEEE 1934 High Performance Serial Bus", Apr. 8, 1999, 18 pages.

* cited by examiner

METHOD AND SYSTEM FOR USING A NEW BUS IDENTIFIER RESULTING FROM A BUS TOPOLOGY CHANGE

This application claims benefit of U.S. Provisional Application No. 60/125,321 filed Mar. 19, 1999.

FIELD OF THE INVENTION

The present invention relates to interconnected systems. In particular, the present invention relates to audio, video, and audio/video interconnected systems for home and office use. More particularly, the present invention relates to a method and system for using a new bus identifier resulting from a bus topology change.

BACKGROUND OF THE INVENTION

With the development of consumer electronic audio/video (A/V) equipment, and the advance of digital A/V applications, such as consumer A/V device control and signal routing and home networking, various types of data in various formats can now be transferred among several audio/video control (AV/C) devices via one digital bus system. However, many current systems do not have sufficient bandwidth resources to transfer and display all the different types of data at the same time.

Typical computer systems solve the bandwidth problem by increasing the bandwidth of the system bus to handle all of these forms, types and amount of data. As a result, as users request more types of information such as in multimedia applications, the system bus has become more clogged with information other than information directly utilized and needed by the main processor.

Many computer systems incorporate at least two buses. A first bus, commonly referred to as a memory bus, is typically used for communications between a central processor and a main memory. A second bus, known as a peripheral bus, is used for communications between peripheral devices such as graphics systems, disk drives, or local area networks. To allow data transfers between these two buses, a bus bridge is utilized to "bridge" and thereby couple, the two buses together.

One example of a high-speed bus system for interconnecting A/V nodes, configured as a digital interface used to transport commands and data among interconnecting audio/video control (AV/C) devices, is the IEEE 1394 standard serial bus implemented by IEEE Std 1394-1995, *Standard For A High Performance Serial Bus*, Aug. 30, 1996 (hereinafter "IEEE 1394 standard") and other related 1394 standards.

The IEEE 1394 standard is an international standard for implementing a high-speed serial bus architecture, which supports both asynchronous and isochronous format data transfers. The IEEE 1394 standard defines a bus as a non-cyclic interconnect, consisting of bus bridges and nodes. Within a non-cyclic interconnect, devices may not be connected together so as to create loops. Within the non-cyclic interconnect, each node contains an AV/C device, and bus bridges serve to connect buses of similar or different types.

The primary task of a bridge is to allow data to be transferred on each bus independently without demonstrating performance of the bus, except when traffic crosses the bus bridge to reach the desired destination on the other bus. To perform this function, the bridge is configured to understand and participate in the bus protocol of each of the buses.

Multi-bus systems are known to adequately handle large amounts of information. However, communication between buses and devices on different buses is difficult. Typically, a bus bridge may be used to interface I/O buses to the system's high-performance processor/memory bus. With such I/O bridges, the CPU may use a 4-byte read and write transaction to initiate DMA transfers. When activated, the DMA of a serial bus node generates split-response read and write transactions which are forwarded to an intermediate system backbone bus that also implements serial bus services.

Depending on the host system design, the host-adapter bridge may have additional features mandated by differences in bus protocols. For example, the host bus may not directly support isochronous data transfers. Also, the host-adapter bridge may enforce security by checking and translating bridge-bound transaction addresses and may often convert uncached I/O transactions into cache-coherent host-bus transaction sequences.

A common occurrence in multi-bus systems is a bus topology change. For example, a bus topology change may occur if a device is added or removed on a bus. Such a bus topology change causes a bus reset in which the bus topology is reconfigured. In the bus reset process, three procedures are typically performed, which are bus initialization, tree identification, and self-identification. Consequently, the bus reset process may affect local or physical address ("phyID") of devices on the bus.

Typically, an address for a device on the bus includes a bus identifier ("busID") and a local identifier ("phyID"). The busID identifies a particular bus in the multi-bus system, and the phyID identifies where the device is located on the particular bus. For example, a device may have a busID and a phyID of "x.0" in which "x" indicates the busID and "0" indicates the phyID.

In prior multi-bus systems, the self-identification procedure of the bus reset provides the phyID for devices on the affected bus, and the busIDs are maintained. The busIDs are maintained to provide busID stability. For example, before a bus reset, a device may have a busID and a phyID of "x.0," and after the bus reset the busID and phyID may change to "x.3." Hence, in prior multi-bus systems, a conversion table is required to convert the address "x.0" to "x.3" so that the proper device is addressed.

A disadvantage of using conversion tables is that it requires additional hardware and time to perform the conversion process. Another disadvantage of prior multi-bus systems is that the bus reset is contained locally, and devices on other buses cannot be easily and reliably informed of bus reset changes. As such, a device on one bus may incorrectly address a device on another bus that has performed a bus reset. Furthermore, in prior multi-bus systems, a device may have accessed another device in one state before a bus reset, and may try to access the same device after a bus reset in which its state may have changed. Thus, a device may access a device without knowing its change of state.

SUMMARY OF THE INVENTION

A method and system for using a new bus identifier in an interconnect are disclosed. For one embodiment, the interconnect includes a plurality of nodes and at least one bus bridge. A configuration change is determined on the first bus connected to the plurality of nodes. Each node has a corresponding bus identifier. A new bus identifier is assigned for each node having a changed state if a configuration change is determined on the first bus.

The method and system using a new bus identifier allows a node to become aware that another node has a change of state as a result of a configuration change on a bus. Thus, nodes are prevented from unintentionally accessing a node without knowledge of a change of state.

BRIEF DESCRIPTION OF THE DRAWINGS

The present invention is illustrated by way of example and not limited in the figures of the accompanying drawings, in which like references indicate similar elements and in which.

DETAILED DESCRIPTION

A method and system for using a new bus identifier in an interconnect are described. For one embodiment, the interconnect includes a plurality of nodes and at least one bus bridge. A configuration change is determined on the first bus connected to the plurality of nodes. Each node has a corresponding bus identifier. A new bus identifier is assigned for each node having a changed state if a configuration change is determined on the first bus.

In the following description, for purposes of explanation, numerous details are set forth in order to provide a thorough understanding of the present invention. However, it will be apparent to one skilled in the art that these specific details are not required in order to practice the present invention. In other instances, well-known devices and components connected with data buses are shown in block diagram form in order not to obscure the present invention.

Figure 1:
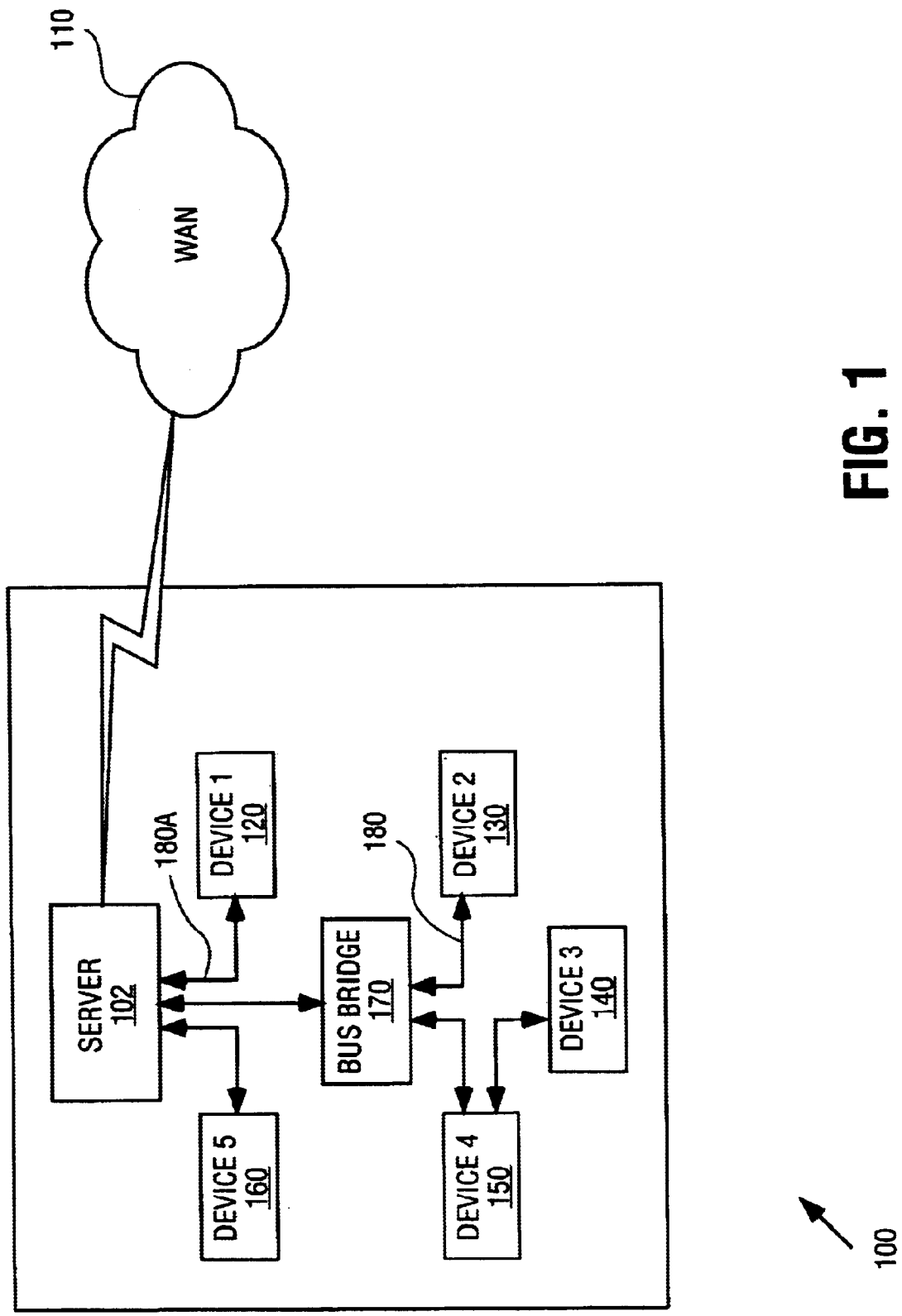
FIG. 1 is a block diagram of one embodiment for an interconnect topology.

FIG. 1 is a block diagram of one embodiment for an interconnect topology 100. Referring to FIG. 1, server 102 is connected to a wide area network (WAN) 110 and to a bus bridge 170. The bus bridge is interconnected to a number of audio, video, and/or audio/video devices, 120, 130, 140, 150, and 160. In one embodiment, the devices (120–160) are connected to bus bridge 170 via the IEEE 1394 standard serial bus. Server 102 may be any device that is capable of connection to both a bus bridge 170 and wide area network 110, such as, for example, a personal computer or a set-top box. In one embodiment, network 110 may be a wide area network, such as, for example, the Internet, or a proprietary network such as America Online®, Compuserve®, Microsoft Network®, or Prodigy®. In addition, WAN 110 may be a television communications network. Server 102 includes a network interface which communicates with WAN 110.

Topology 100 includes high speed serial bus 180a and 180b. In one embodiment, serial bus 180 is the IEEE 1394 standard serial bus. Topology 100 includes various consumer electronic devices 120–160 connected via the high speed serial bus 180 to bus bridge 170. The consumer electronic devices 120–160 may include, for example, a printer, additional monitor, a video camcorder, an electronic still camera, a video cassette recorder, digital speakers, a personal computer, an audio actuator, a video actuator, or any other consumer electronic device that includes a serial interface which complies with a serial interface standard for networking consumer electronic devices—for example, the IEEE 1394 standard. Topology 100 may be contained within a home or office. Bus bridge 170 is used to connect devices 120–160 in which devices 120–160 may be physically located within different rooms of the home or office. Although the original IEEE bus standard is designed for use with a cable interconnect, any communication media may be used such as radio frequency (RF) communication or the like.

Figure 2:
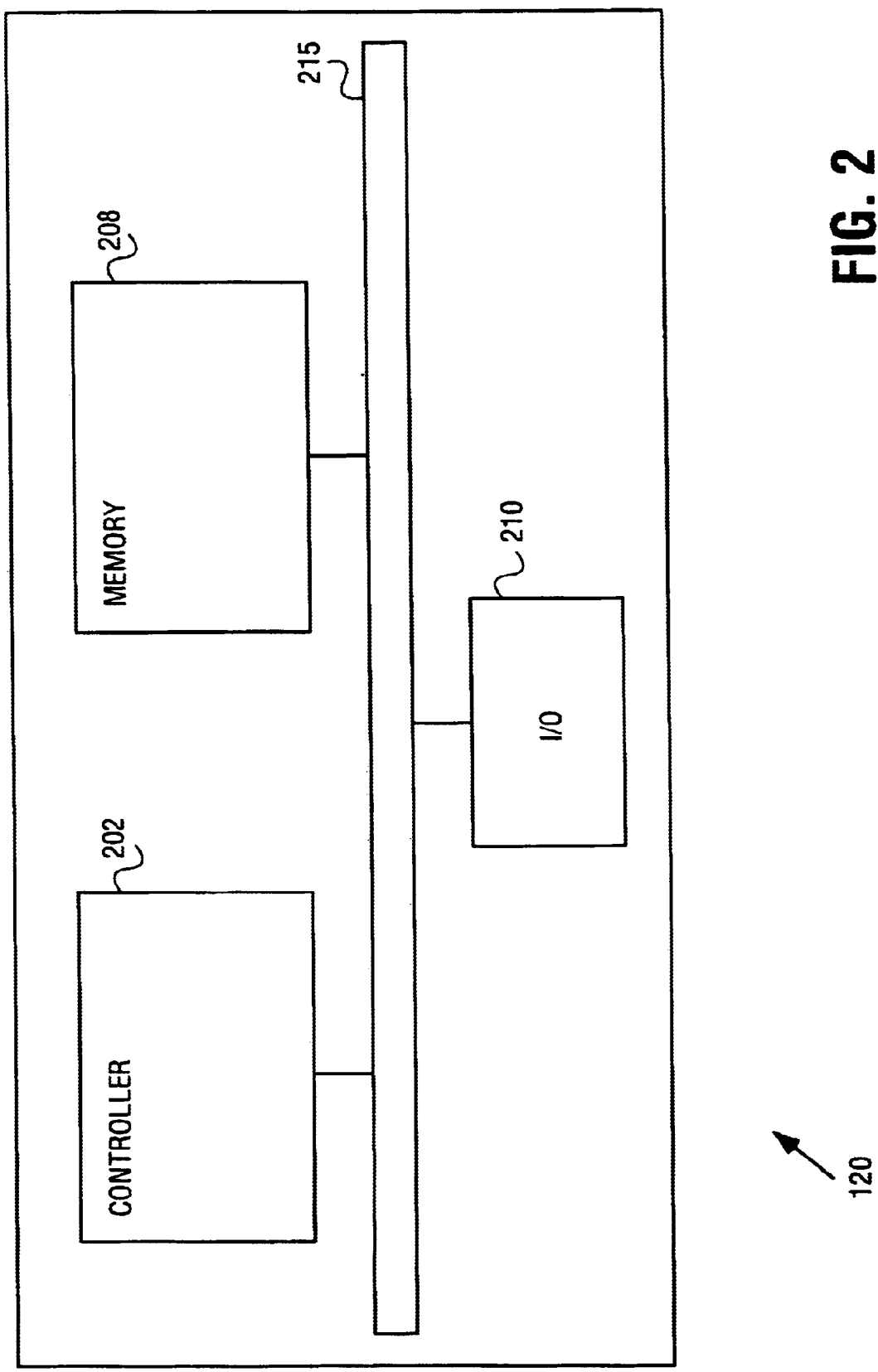
FIG. 2 is a block diagram of a device of FIG. 1.

FIG. 2 is a block diagram of a device 120. Referring to FIG. 2, device 120 may be a laser printer, digital camera, set-top box, or any other appropriate consumer electronic device capable of being connected via a high speed serial bus 180. In one embodiment, the device 120 includes a controller 202, memory 208, and I/O 210, all connected via bus 215. Memory 208 may include, for example, read only memory (ROM), random access memory (RAM), and/or non-volatile memory. I/O 210 provides connection with wide area network 110, bus bridge 170, and another peripheral device (130–160).

In one embodiment, I/O 210 is a serial bus interface that complies with a serial interface standard for networking with consumer electronic devices (120–161) and bus bridge 170 within topology 100. For example, the serial bus interface and topology 100 may use the IEEE 1394 standard serial bus. I/O 210 provides for receiving signals from and transmitting signals to other consumer electronic devices (130–160) or bus bridge 170.

Memory 208 provides temporary storage for voice and data signal transfers between outside network 110 and topology 100. In addition, memory 208 may buffer digital voice and data signals received by I/O 210 from WAN 110 before signals are transmitted onto IEEE 1394 standard bus 180. Controller 202 controls various operations of device 120. Controller 202 monitors and controls the traffic through the device 120 to and from topology 100 and WAN 110.

Device 120 I/O 210 may have one or more physical ports. A single port device discontinues the bus along the given branch of the bus, whereas devices with two or more ports allow continuation of the bus. Devices with multiple ports permit a daisy chained bus topology, even though the signaling environment is point-to-point. That is, when a multi-port node receives a packet of data, the data is detached and retransmitted to the necessary port as indicated within the data. The configuration is performed dynamically as new devices are attached and/or removed from bus 180.

The 1394 standard bus protocol is designed to support peer-to-peer transfers between devices. This allows serial bus devices to transfer data between themselves without intervention from a computer system or host system. This allows high throughput between devices without affecting the performance of the computer system. Thus, a video camera may be set up to transfer between itself and a video cassette recorder without accessing a computer system.

Figure 3:
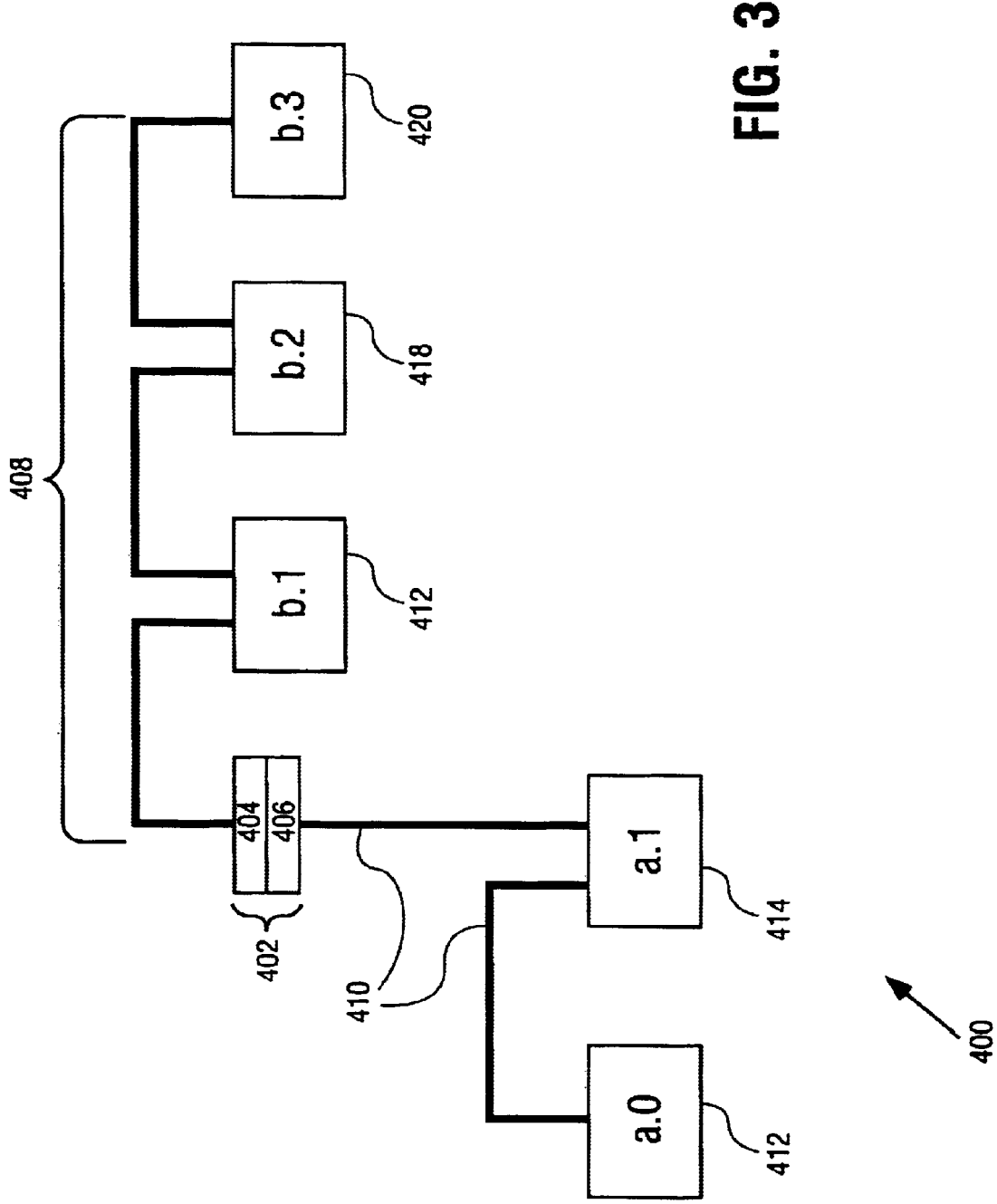
FIG. 3 is a block diagram of one embodiment for a 1394 standard bus bridge system.

FIG. 3 is a block diagram of one embodiment for a 1394 standard bridge bus system 400. Referring to FIG. 3, system 400 includes bridge 402 which connects two or more buses 408 and 410. Bus 408 and 410 may be the same or different types of buses. For example, bus 408 may be a 1394 standard serial bus and bus 410 may be a different high performance bus. The 1394 standard bus architecture limits the number of nodes or devices 416, 418, 420 on a bus 408 and supports multiple bus systems via bus bridge 402.

The control and status register (CSR) architecture, ISO/IEC 13213 (ANSI/IEEE 1212), *Information systems-Control and Status Registers (CSR) Architecture Microcomputer Buses*, defines the 1394 standard bus addressing structure, which allows approximately $2^{16}$ nodes (404, 406, 412–420). The CSR standard defines their registry, their functionality, and, where appropriate, where they appear in the address space.

Figure 4:
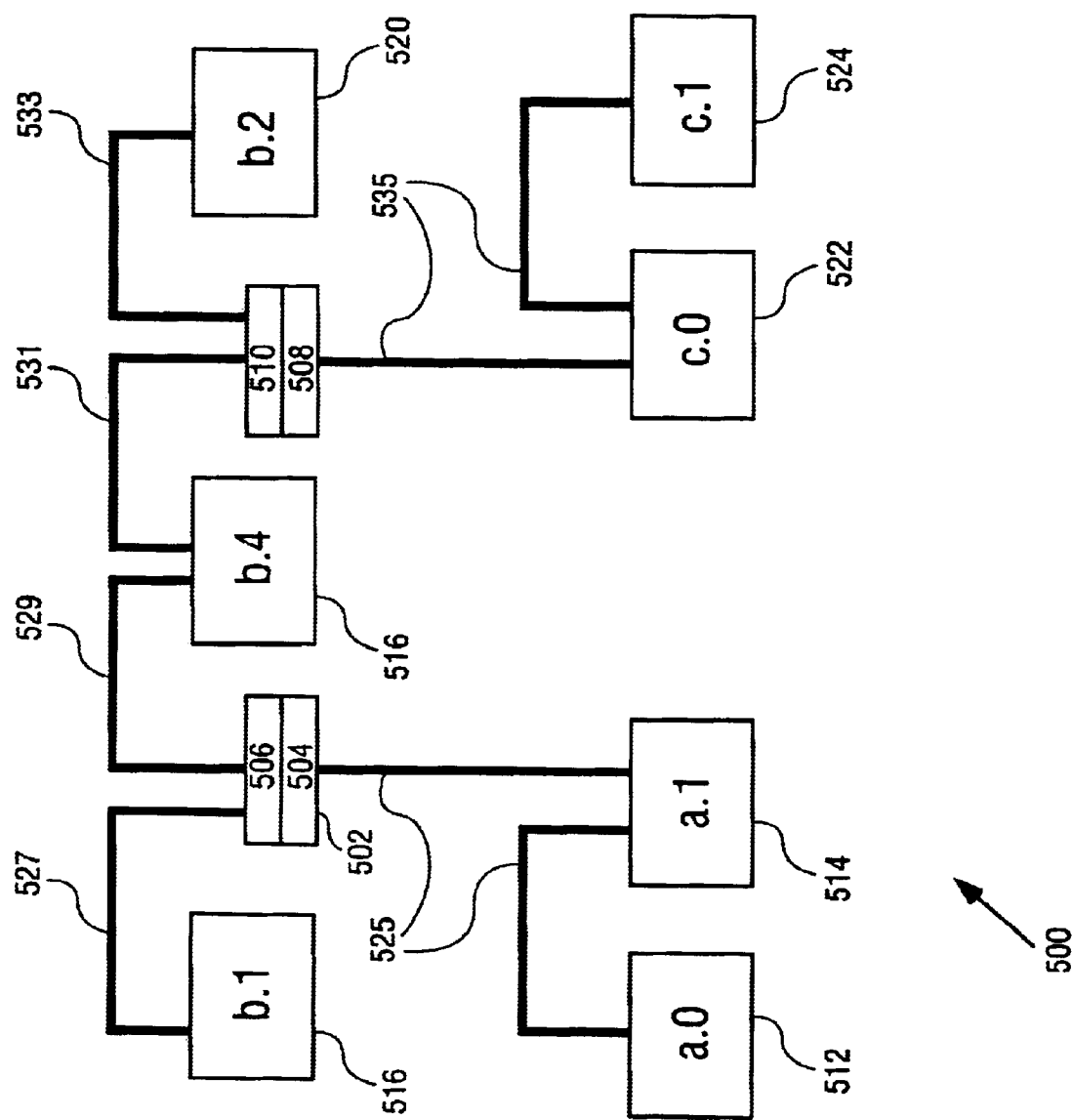
FIG. 4 is a block diagram of one embodiment for a 1394 bus bridge topology.
Figure 5:
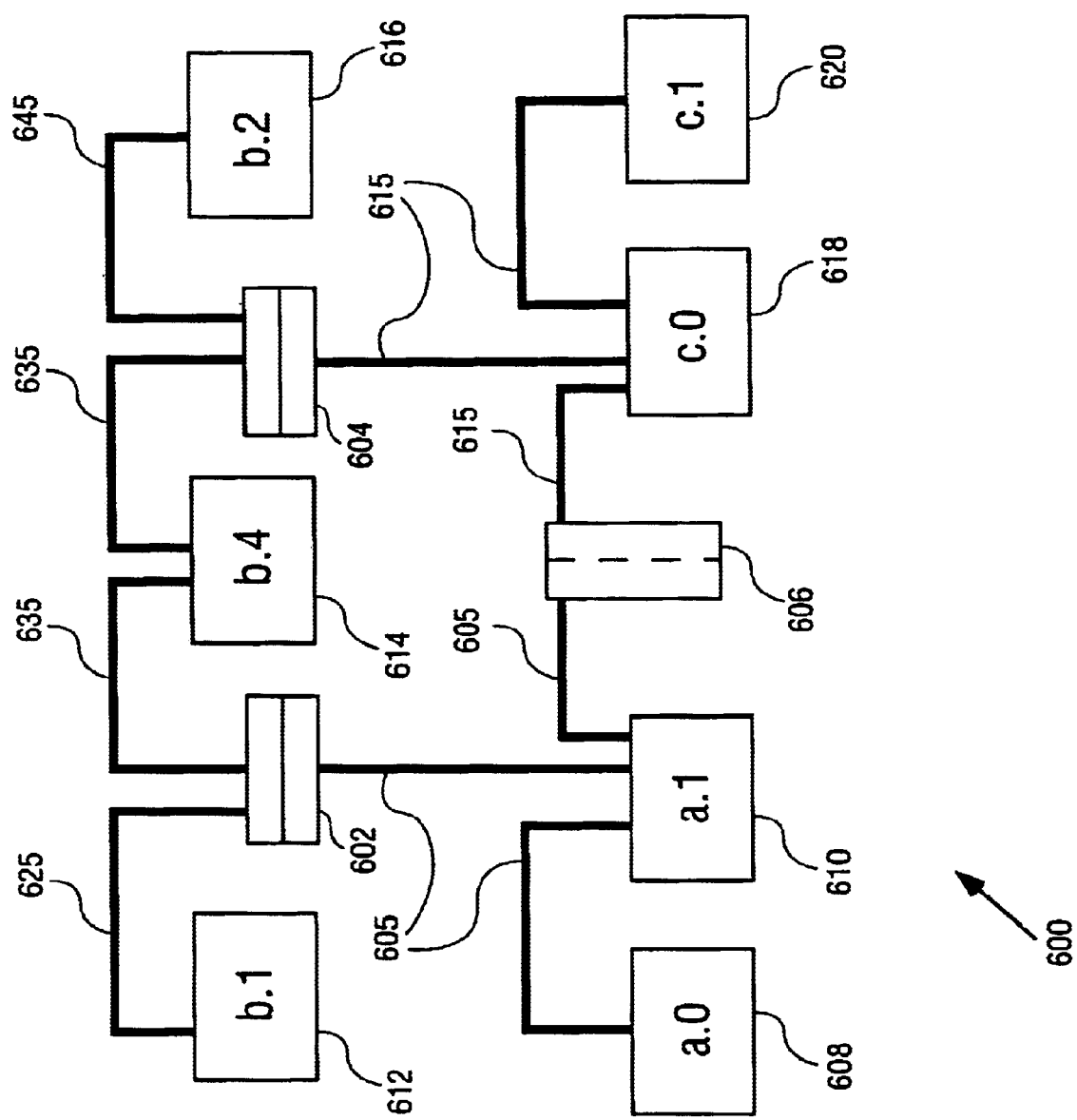
FIG. 5 is a block diagram of one embodiment for a looped bus bridge topology.

FIG. 3 is the simplest instance of a bus topology in which the net has one bus bridge. FIG. 4 illustrates a net that may have more than one bus bridge and, when so structured, is hierarchical in nature. FIG. 5 illustrates a network whose physical topology may have loops, but whose loops are electronically disabled to generate a hierarchical structure. In the description that follows, a collection of multiple buses connected through a bus bridge is referred to as a "net".

FIG. 4 is a block diagram of one embodiment for a 1394 bridge bus topology 500. Referring to FIG. 4, topology 500 has one prime portal 504 and one or more alpha portals 506 and 508. The primary bus 525 has exactly one prime portal 504 and the secondary buses 527, 529, 531, 533, and 535 have exactly one alpha portal each—506, 508 and 510. Each bus 525–535 may have any number of secondary portals. An alpha portal is on the path to a prime portal. Any portal not a prime portal or an alpha portal is a secondary portal. The prime portal or the alpha portal may be referred to as a primary portal.

Within an interconnect topology 500, the bridge portal with the largest refresh ID identifier is elected to become the prime portal 504. In an alternate embodiment, the bridge portal with the smallest refresh ID identifier is elected to become the prime portal 504. Each portal appears as a node on its attached bus. The bus with the prime portal 504 is termed the primary bus 525 and other buses 527–535 are termed secondary buses. On secondary buses 527–535, the bridge portal that leads to the primary bus 525 is called the alpha portal (506, 508). After a bridge bus interconnect is configured, any node within the interconnect may be accessed by its unique 16-bit node identification address. The node identification address contains the bus ID and the local ID components. Referring to FIG. 4, the bus identification IDs of nodes 512–524 are indicated by the letters a, b, and c and the local ID is indicated by the numbers 0–4.

In one embodiment, alpha portal 504 is responsible for rejecting missed address asynchronous data packets by accepting these requests and returning error reporting responses. The previous and current prime and alpha portal identifiers are used to classify nodes when an interconnect topology changes, and the alpha portal is the isochronous clock reference for other nodes on the bus.

Bus bridge topology 500 may change and be established dynamically during operation of bus bridge system 500. In one embodiment, the bus bridge topology 500 is established during net refresh. Within topology 500, portals selectively route packets. Asynchronous routing tables are stable until topology 500 changes during a net refresh or net reset operation. Asynchronous routing tables are dynamic and are changed by their asynchronous connect and disconnect operations of the protocols.

FIG. 5 is a block diagram of one embodiment for a looped bus bridge topology 600. The bus bridge topology 600 includes portals 602, 604, and nodes 608, 610, 612, 614, 616, 618, 620. The bus bridge topology 600 further includes buses 625, 635, and 645. Referring to FIG. 5, portal 606 may be added to the topology 600 forming a loop. Thus, a path exists from a0–b4 through c0 back to a0. During initialization, the redundant portal 606 is disabled so that a hierarchical bus bridge topology remains.

In an alternate embodiment, cyclical net topologies may be allowed. In this alternate embodiment, software routines may partially activate the redundant bridge 606 and allow a shortest path routing between nodes. For example, traffic between bus a 605 and bus c 615 may be efficiently routed without introducing deadlocks.

Figure 6:
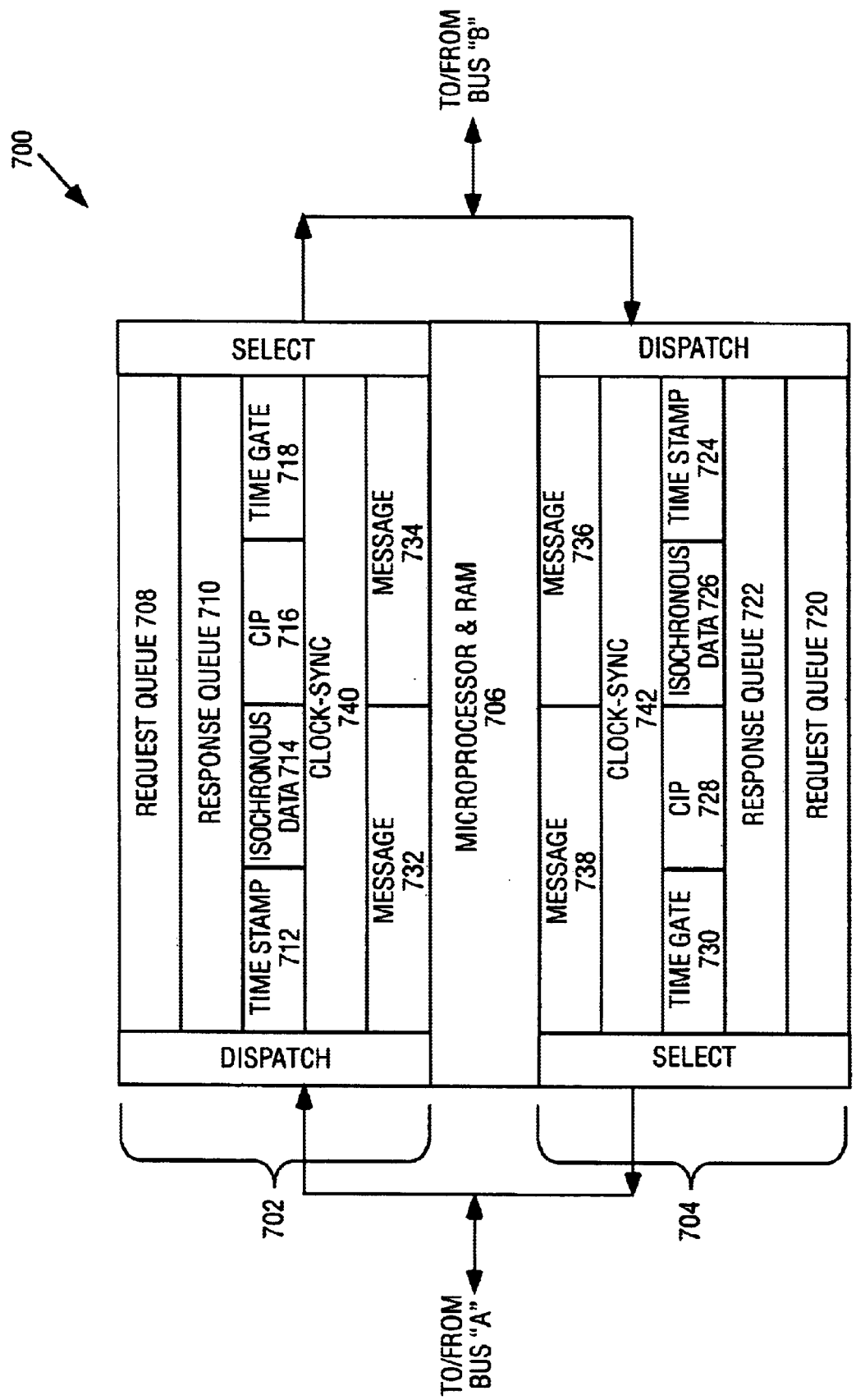
FIG. 6 is a block diagram of one embodiment for bus bridge components.

FIG. 6 is a block diagram of one embodiment for bus bridge components 700. Referring to FIG. 6, bus bridge components 700 are maintained within each portal in which bus "a" to bus "b" components 702 and bus "b" to bus "a" components 704 are independently maintained. Components 700 also contains shared microprocessor and RAM 706.

Asynchronous and isochronous packet transfers may not acquire a bus at the same time. Therefore, asynchronous packets are placed in request queues 708, 720 and response queues 710, 722. The asynchronous packets are selected for transfer at times when isochronous packets are not being transferred. Isochronous packets are received and time stamped 712, 724. Time gates 718, 730 release the isochronous packets 714, 726, together with common isochronous packet (CIP) headers 716, 728, at fixed times. Routing tables select which asynchronous and isochronous packets are accepted and queued for adjacent bus delivery.

Topologies may share physical buffer space rather than implementing physical distinct stacks subject to the following: bus "a" to bus "b" and bus "b" to bus "a" queues operate independently, response processing is never blocked by queued requests, and asynchronous subactions and isochronous packets are forwarded independently. Topologies may block a request behind the previously queued response without generating potential deadlocks; however, requests and responses are processed independently.

Isochronous routing decisions are made by checking the isochronous packet's channel number. Accepted packets are converted and retransmitted on the adjacent bus with newly assigned channel numbers, speeds, and CIP-header and, when a CIP-header is provided, time-stamp parameters 716, 728 from the CIP-header. CIP-headers may be pre-appended to some isochronous packets to further describe their format and function and desired presentation time. When the packets incur delays while traversing through a bridge, then presentation time must be adjusted to compensate for this delay. CIP headers are defined in ISO/IEC 61883 specification. Isochronous packets received in cycle n are forwarded to the adjacent bus in cycle n+k where k is an implementation dependent constant. Messages may be passed around one bus or pass through a bridge by writing to a standardized message location 732, 734, 736, 738 on a bridge's portal. This allows bus-interconnect topologies to be restored while freezing, or discarding when necessary, previously queued subactions.

Distribution of clock-sync information 740, 742 from the primary-bus source is performed by placing calibration information in isochronous-clock pseudo queues before forwarding this information to the clock master on the adjacent portal. In one embodiment, clock-sync information flows from the primary bus downward, so that only one clock-sync pseudo queue may be required.

In support of bus bridges, each node has two node ID addresses: physical ID address and virtual ID address. A physical node ID has a $3FF_{16}$ valued bus ID; a virtual node ID has smaller bus ID addresses. In the absence of bus bridges, all nodes are accessed through their physical addresses. In the presence of bus bridges, the physical address is used to configure the node and the virtual address is normally used thereafter.

Directed-asynchronous routing decisions are made by checking the destination ID addresses of pass-through packets. Accepted packets are directly routed to the bridge's opposing port. In addition, an asynchronous quarantine is maintained which selectively enables forwarding of a request sub-action based on the local identification of a bus-local requester. A set of legacy bits identifies local nodes which requires specific processing of sourced requests and returning responses.

Figure 7:
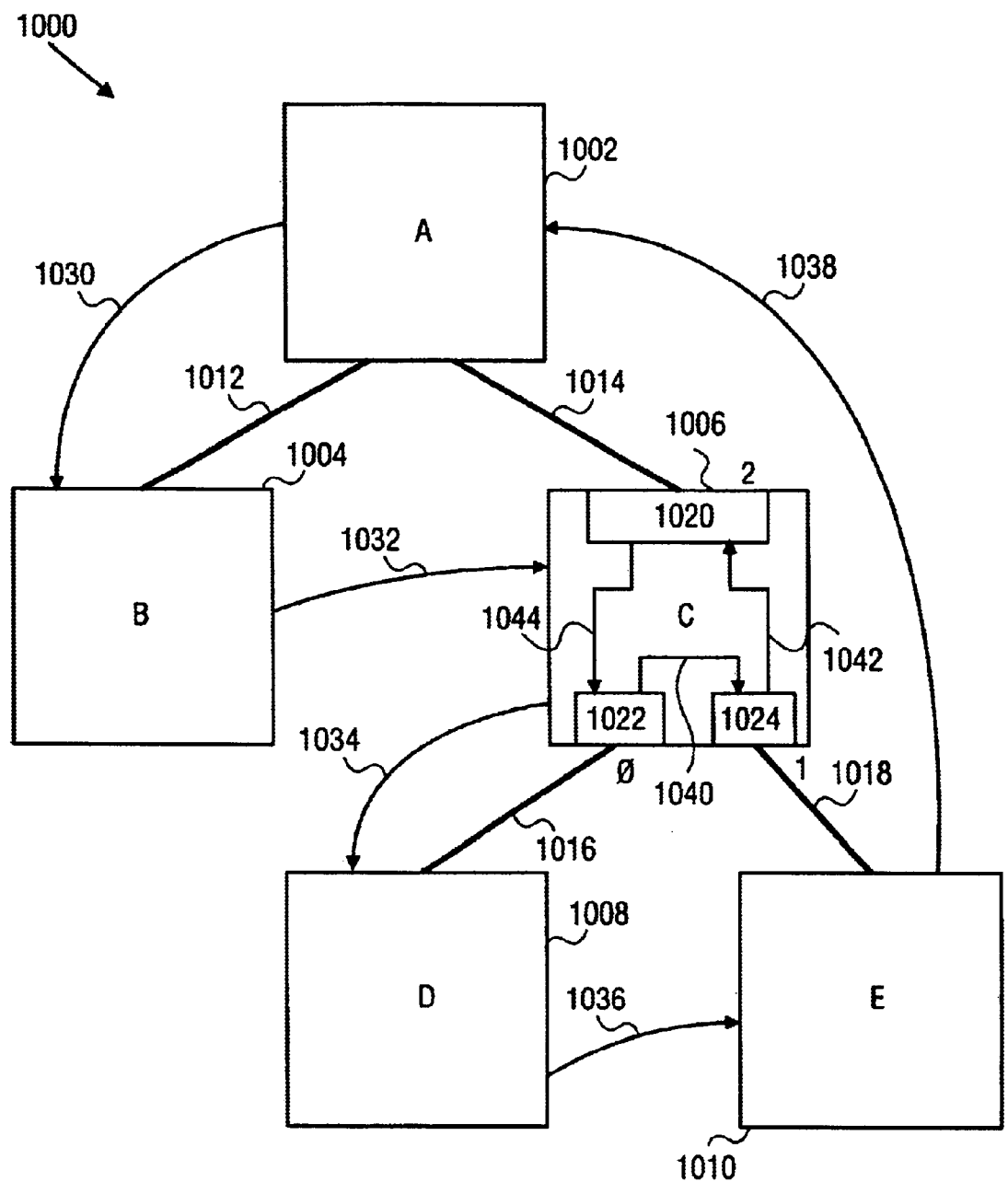
FIG. 7 is a block diagram of one embodiment for a next-neighbor ordering topology.

FIG. 7 is a block diagram of one embodiment for a next-neighbor ordering topology 1000. Referring to FIG. 7, topology 1000 contains a number of nodes 1002, 1004, 1006, 1008, and 1010 connected through respective buses 1012, 1014, 1016, and 1018. Each node 1002–1010 is defined by a relative ring identification (ringID) value made up of the bus identification (busID) and physical identification (phyID) portions. Each node 1002–1010 defines its next neighbor by the relative ringID values in which each node derives the ringID value from the observed self identification (selfID) packets. In one embodiment, a mapping is applied to selfID (packets) in order to arrive at a phyID to ringID mapping. During the self-identify process, each node uniquely identifies itself (selfID), maps its selfID to ringID, and uses its ringID to communicate with its topologically adjacent node.

In one embodiment, the assignment of ringID values is based on a conceptual routing of signals through a node's ports. Using node C 1006 as an example, port[a] 1022 identifies physical port 0, port[b] 1024 identifies physical port 1, and port[c] 1020 identifies physical port 2. Ports 1020–1024 have an implied internal ordering as follows:

port[a].in→port[b].out 1040
port[b].in→port[c].out 1042
port[c].in→counter→port[a].out 1044

In one embodiment, each node 1002–1010 assigns conceptual ringID values to the other nodes, starting with ringID=0 on its own port[a] 1022 output. The ringID values are assigned by logically tracing a path through other physical ports, incrementing the ringID when logically passing through the port[a] 1022 output.

The bus itself defines protocols for sending selfID packets for purposes of assigning unique phyIDs to each of the attached nodes. Although phyIDs are guaranteed to be unique, they are not guaranteed to be the same if the bus is reset again. Thus, there is a need for defining ringIDs which do not change unless the cable topology actually changes.

This assignment strategy always yields the same next-neighbor selections, despite changes in the selected-root assignment or a change in the root node. Thus, in the example shown in FIG. 7, node B 1004 determines that node C 1006 is its next neighbor, node C 1006 determines that node D 1008 is its next neighbor, node D 1008 determines that node E 1010 is its next neighbor, node E 1010 determines that node A 1002 is its next neighbor, and node A 1002 determines that node B 1004 is its next neighbor. The topology, rather than the physical nodes, is traced by following paths 1030, 1032, 1034, 1036, and 1038 from a port to its next neighbor, and any node 1002–1010 may be used as the root.

Figure 8:
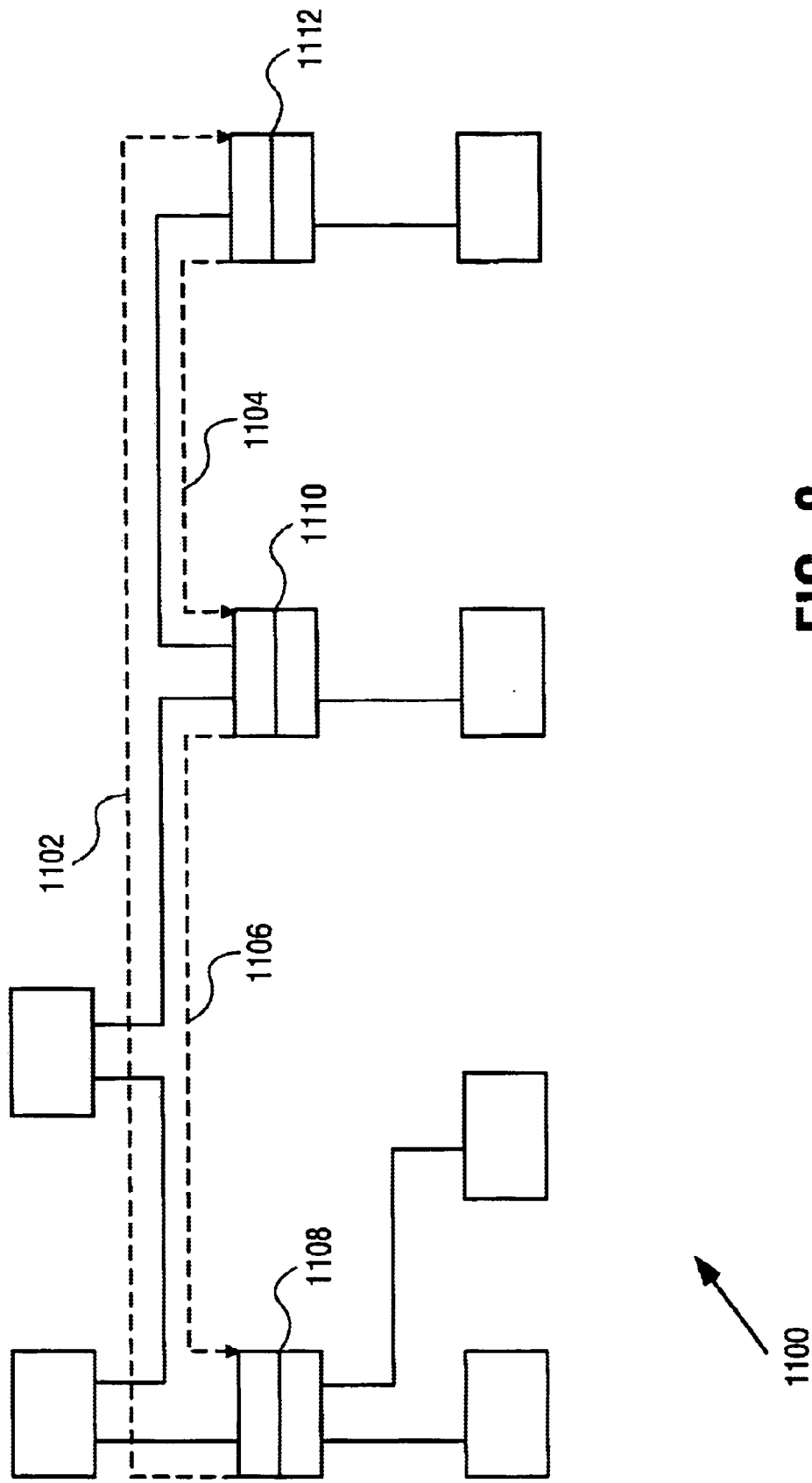
FIG. 8 is a block diagram of one embodiment for a portal-to-portal net refresh message path topology.

FIG. 8 is a block diagram of one embodiment for a portal-to-portal net refresh message path topology 1100. A net refresh is used to assign unique busIDs to each node in the system. Referring to FIG. 8, the communication protocols for net refresh involve the sending of messages from each portal 1108, 1110, 1112 to its neighbor in a daisy-chained fashion. In one embodiment, these responseless write messages are idempotent, so that missing-ack failures may be simply and safely retried (e.g. multiple writes have the same effect as one write).

A net refresh is typically triggered by a bus reset. After the bus reset completes, each portal 1108, 1110, 1112 sends messages to its next neighbor, allowing messages to flow in a circular direction. Thus, the topology-dependent, root-independent portal ordering is available after bus reset. This allows each portal 1108–1112 to circulate messages by sending them in a next-neighbor ordering.

In the example shown in FIG. 8, portal 1108 first sends a message via path 1102 to portal 1112, portal 1112 then sends a message via path 1104 to portal 1110, and finally, portal 1110 sends a message via path 1106 to portal 1108. In this context, "next" means the portal with the next larger ringID assignment.

In one embodiment, a 2-bit precedence is pre-appended to the portal's 64-bit extended unique identifier (EUI) to generate a stable refresh identifier (refreshID). The prime portal's EUI also serves as the context identifier for bridge routing tables. The refreshID allows topology 1000 to specify prime-portal preferences. To coordinate activities when resets occur on multiple buses, a prime portal is selected to coordinate the net refresh activities. In any net, the local-bus portal with the largest refreshID is selected to become the net's prime portal.

Write messages that incur errors or busy indications are immediately retried until successful. Confirmations are provided by allowing these write messages to circulate through other portals until they return to the origin portal. The constant sending of these responseless write messages ensures their successful completion without mandating special fault-retry protocols. The circular nature of the communication allows the originator of these write messages to verify their completion. Such communications are sufficient for reliable broadcasts, but are more flexible because write payloads may be modified as they pass through connected portals.

In one embodiment, a bus reset may occur when a new node is attached to the net. The bus reset has the effect of invalidating the bus ID address contained within the node ID registers of local portals, which effectively isolates them from the remaining portion of the net. A net refresh acquires a new bus number for the reset bus without affecting the busID addresses or routes of other portals.

A net refresh starts with messages sent between local bus bridge portals. A prime-portal is selected to coordinate the net refresh operation. Each node sends acquisition messages to its next neighbor, and these messages initially contain refreshID (a prime-portal selection identifier). Each candidate portal monitors incoming refreshID values and changes to a subservient portal when a larger refreshID is observed. In one embodiment, the largest refreshID value eventually circulates to all local portals, as illustrated by FIG. 8. In alternate embodiments, other refreshID values may be used to determine the prime-portal. The acquisition message supplies the refreshID, as well as a bus Count and portal Count.

The portal Count value in the acquisition messages is incremented when passing through the portals. This ensures the eventual demise of rogue resets, by allowing them to be aged until dead. Reset messages are sent periodically, once each arbitration interval, until the net refresh completes. In the absence of continuous messages, portals time out and attempt to become prime portals.

The net refresh eventually forms a spanning tree by circumscribing the paths through bus bridge portals 1108–1112. Each portal communicates with its adjacent neighbor by writing messages into a standardized control and status register (CSR) location. During the final state of a net refresh, the portal-to-portal messages flow in the direction of paths 1102, 1104, and 1106.

At the conclusion of the net refresh, each node has a net-unique nodeID consisting of busID and localID components. A node's localID equals its phyID. In addition, each portal has a distinctive portal identifier (portalID) that may be used to navigate through the topology.

In one embodiment, a net-changed indication is broadcast to all nodes during a net refresh. As no packets are corrupted if this notification is ignored, the system is not compromised by these unconfirmed broadcast indications. This event notification allows nodes to determine when bus numbers have changed or when audio/video (AV/C) controller reconnections are required. AV/C protocols are used to establish, monitor, and release isochronous connections as required. The net-changed event is bus-local and is sent during net refresh. Since all portals are communicating with others during net refresh, the coordination of these bus-local resets comes out of the net-refresh sequencing. During the net refresh, each of the dominant (prime or alpha) portals is responsible for distributing the net-changed event indication to locally attached secondary portals.

One of the reasons for invoking a net refresh is to resolve inconsistent or ambiguous non-local isochronous resource allocations. The listener and talker proxies assume this obligation, allowing resources to be reclaimed (or lost) in a timely fashion.

A net refresh refers to the sequence of actions that assign busID addresses and establish the bus bridge routing tables. The term net refresh is used because the effects of a net refresh on the bridge portals within the net are similar to, but less disruptive than, the effects of a bus reset on the nodes attached to the bus.

In one embodiment, the net refresh maintains the previous busID assignments, bridge portal routing tables, established isochronous channels, and queued subactions.

A configuring net refresh (often abbreviated as configuring refresh) has the effect of assigning non-conflicting busID addresses to each of the attached buses. When busIDs conflict, either with a currently assigned busID or a DIRTY (previously assigned) busID, new FREE busIDs are assigned.

As an example, a configuring refresh occurs on the surviving portion of a severed net (assuming that a sufficient number of FREE-state busIDs remain).

A cleansing net refresh (often abbreviated as "cleansing refresh") has all of the properties of a configuring refresh and (in addition) initiates the DIRTY-to-FREE recycling of stale busIDs by setting quarantines in each bus-bridge portal. After the quarantines have been set, the portal can recycle DIRTY busIDs after a time delay of $T_{dirt}$. The $T_{dirt}$ value is the maximum time a transaction can remain queued before passing out of the bus bridge.

A cleansing refresh is typically performed when the number of DIRTY busIDs exceeds the number of FREE busIDs. The intent is to recycle the DIRTY busID states, to avoid the invocation of a more disruptive purging net refresh. A net refresh is also invoked on the victim portion of a severed net, to reduce the disruption of survivor subnet buses when the victim and survivor sub-nets are reconnected.

A purging refresh is performed when the number of desired busIDs exceeds the number of FREE busIDs. Although a cleansing refresh would eventually change busIDs from DIRTY-to-FREE, the purging refresh avoids the delay associated with the cleansing-refresh recycling process.

Since bus bridges may have previously-queued transactions with DIRTY-state busID addresses, these queues are purged. This occurs quickly and without timeout-related delays, with the disadvantage of disrupting currently-active transactions.

During the net refresh, nodes communicate the parameters related to in $T_{dirt}$ in net refresh messages so as to compute the worst case values. The maximum number of hops, N, between any requester and any responder is also computed and distributed to portals during net refresh.

Figure 9:
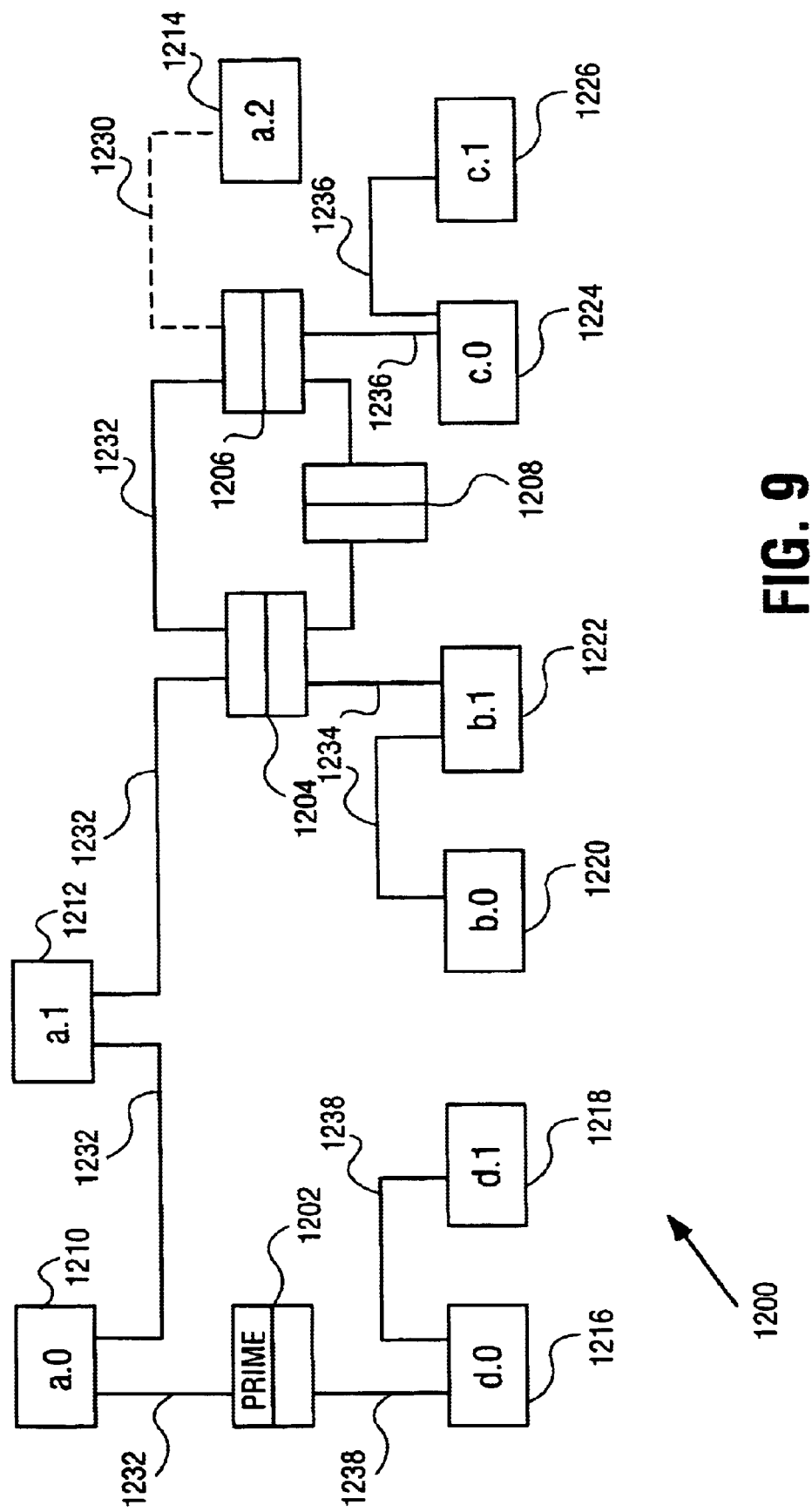
FIG. 9 is a block diagram of one embodiment for a net refresh message path topology during the addition of a node.

FIG. 9 is a block diagram of one embodiment for a net refresh message path topology 1200 during the addition of a node. Referring to FIG. 9, topology 1200 consists of prime portal 1202, alpha portals 1204, 1206, 1208, primary bus 1232, secondary buses (1238, 1234, and 1236), existing nodes (1210, 1212, 1216, 1218, 1220, 1222, 1224, 1226) and a node to be attached 1214.

"Net refresh" refers to the sequence of actions that assigns bus identification addresses and establishes the bus bridge routing tables. The term refresh is used because the effects of a net refresh on the bridge portals in the net are similar to, but less destructive than, the effects of a bus reset on the nodes attached to the bus. Whenever possible, the net refresh maintains the previous bus identification assignments, bridge portal routing tables, establish isochronous channels, and queued sub-actions. A net initialization established the spanning tree as described above for the topology and assigns non-conflicting busIDs.

In one embodiment, three forms of net initialization may be specified: 1) net refresh, which assigns new busIDs, 2) net restart, which is a net refresh plus delayed busID recycling quarantine overhead for recently active requesters, and 3) net reset, which is a net refresh plus immediate busID recycling and transaction termination for currently active transactions. During bus resets, each bridge portal is assumed to be aware of the bridge portal next neighbor with the next larger ringID address as described above. In this embodiment, local daisy chain sequences are possible. For example, portal A sends messages to portal B. portal B sends messages to portal C, and portal C returns messages to portal A.

A net refresh may occur when a new node 1214 is added to the topology 1200 via bus 1230. In one embodiment, a net refresh configures a primary bus 1232 with one primary alpha portal 1202. Other secondary buses (1238, 1234, and 1236) and one alpha portal 1204 are also configured during a net refresh.

Net reset is a multi-phase operation, as discussed in reference to FIGS. 10 and 11 below. In one embodiment, the net reset is accomplished in three stages: the acquire stage, the breach stage, and the commit stage. The initial acquire and breach phases select the prime portal and detect addressing conflicts, while the final commit phase assigns busID assignments, establishes routing tables, and, when necessary, purges asynchronous bridge queues. During the acquire phase, periodic acquisition messages are distributed to other bus local portals. During the breach phase, the acquired portals sequentially extend their acquisitions to adjacent buses. During the commit phase, the prime portal sends commit messages, allowing bus numbers and routing tables to be updated.

Referring to FIG. 9, the addition of node 1214 may invoke a net reset. The net reset invalidates local busID assignments and all reset portals (1202, 1204, and 1206) become prime portal candidates. Each reset portal 1202–1206 attempts to restore its own invalid busID addresses and disables pass-through traffic. In an alternate embodiment, reset portals 1202–1206 may allow local traffic and some amount of pass-through traffic.

During a purging net refresh, topology 1200 is left in a known initial state. Purging refreshes are designed to be robust and timely, which requires them to be more disruptive. The process of initializing net topology 1200 involves formation of a spanning tree by circumscribing the net while passing through bus bridge portals, as illustrated in FIG. 7. For stability, the node with the largest refreshID is selected to become the prime portal (in the examples of FIGS. 10 and 11, it is assumed that portal 1202 becomes the prime portal). The prime portal's refreshID is also used as the context identifier that is distributed among the nodes.

In the discussion that follows, a net refresh is assumed to be initiated by prime portal 1202. However, a net refresh may be initiated by any portal. If a net refresh is initiated by a non prime portal, the initial net refresh messages would eventually propagate the prime portal, which (due to its larger refresh identifier) would become responsible for completing the net refresh, as discussed below.

Figure 10:
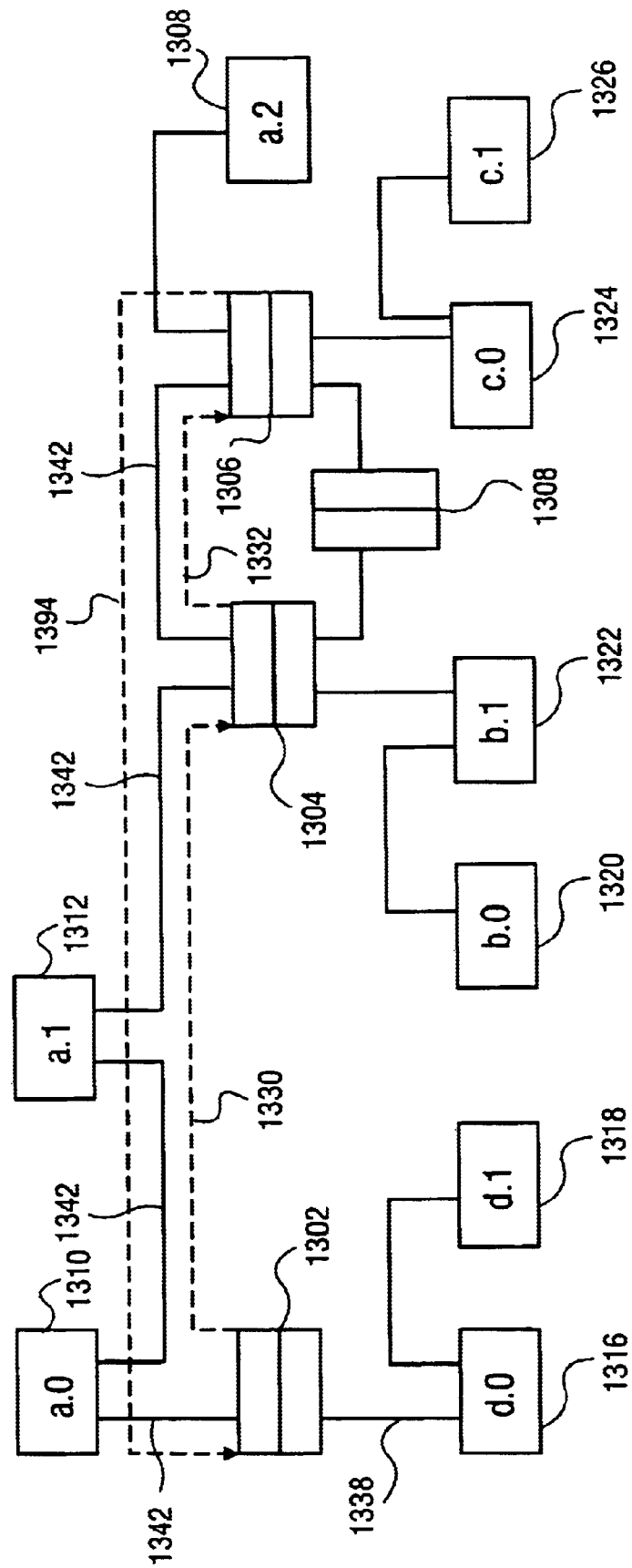
FIGS. 10 and 11 are block diagrams of one embodiment illustrating a purging net refresh.

FIG. 10 is a block diagram of one embodiment illustrating a purging net reset of interconnect 1300. In FIG. 10, the interconnect 1300 includes multiple nodes 1310, 1312, 1316, 1318, 1320, 1322, 1324, and 1326. A net reset may occur when a new node 1314 is attached to interconnect 1300. The net reset has the effect of invalidating portals (1302, 1304, 1306, 1308) nodeID and busID addresses. This has the effect of isolating the portals from external access. In the example of FIG. 10, the net reset on interconnect 1300 is assumed to be initiated by the prime portal 1302. However, all reset bus portals (1302, 1304, 1306, 1308) may act as the prime portal, and the prime portal status is speculative and must be reconfirmed during net refresh (as described in reference to FIG. 7).

A net reset begins with a "reset acquire" message sent between bus bridge portals 1302–1308. The first of these messages is sent from prime portal 1302 and circulates through secondary portals 1304 and 1306 on the primary bus 1342. The message paths are indicated by hash lines 1330, 1332, and 1334, beginning at prime portal 1302.

As discussed above, portalID values in the net reset packets are incremented when passing through the not yet enumerated bus bridge portals (1302–1308). This ensures the eventual demise of rogue resets by allowing them to be "aged until dead." In one embodiment, reset messages are sent periodically, once each arbitration interval, until the net refresh completes. In the absence of a prime portal's resets, other portals may timeout and attempt to become prime portals. Candidate portals (1302–1308) recognize their loss (i.e., not the prime portal) when higher precedence acquire messages are observed, whereupon the portals forward the messages to other portals (next neighbor).

The acquisition of the primary bus completes when the candidate's message returns to the candidate. For example, prime portal 1302 sends a message via 1330 to portal 1304 to acquire bus 1342. The message is passed from portal 1304 via 1332 to portal 1306 and from portal 1306 via 1334 to portal 1302. Once the acquire message returns to portal 1302, portal 1302 acquires its own bus 1342.

Figure 11:
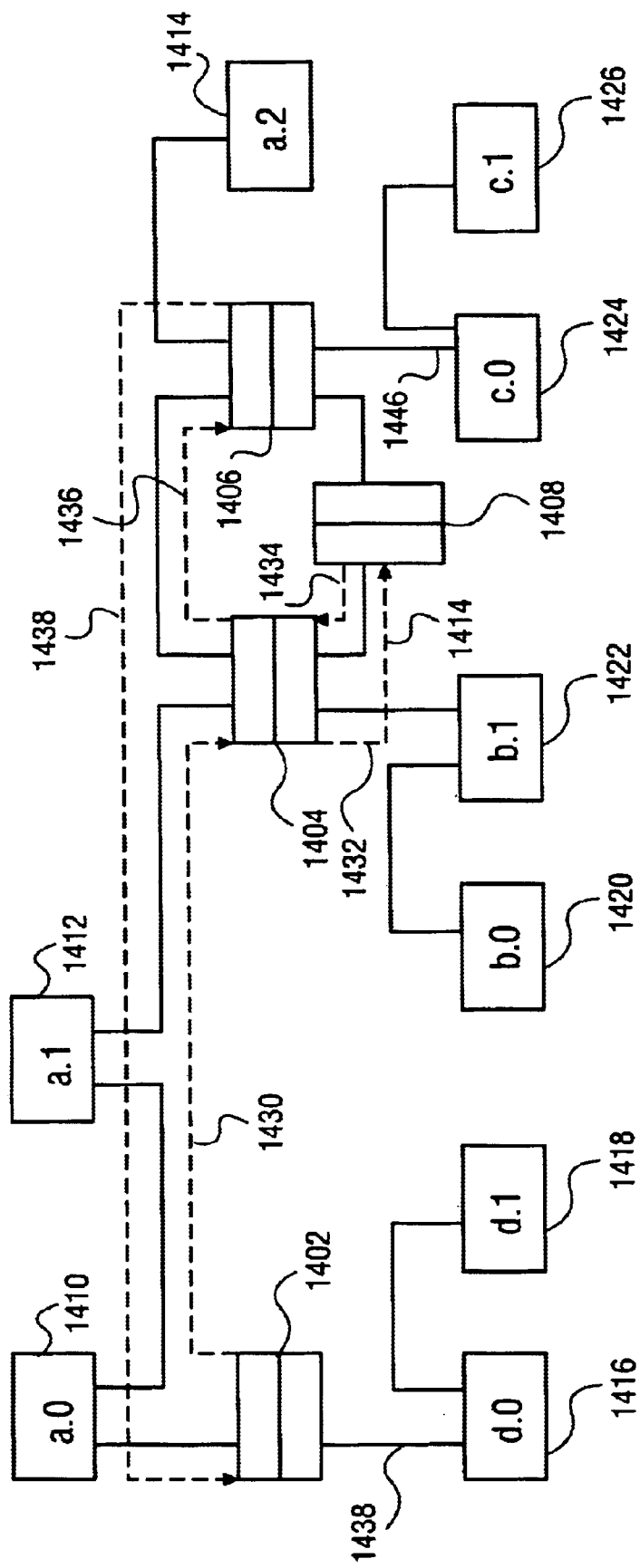

After the primary bus 1342 has been acquired, the prime portal transmits a breach message as illustrated in FIG. 11. In FIG. 11, the interconnect 1400 includes multiple nodes 1410, 1412, 1414, 1416, 1418, 1420, 1422, 1424, 1426, and portals 1402, 1404, 1406, and 1408. Prime portal 1402 transmits a breach message via path 1430 to portal 1404. The receipt of a breach message by portal 1404 causes portal 1404 to breach onto adjacent bus 1444. The breach commands trigger sequential acquisitions of adjacent buses. The reset breach message initiates the acquisition of the first remote bus 1444 as indicated by paths 1432, 1434, 1436, and 1438.

After adjacent buses are acquired, breach packets are sent to initiate a remote bus acquisition. The next portal on the adjacent bus observes the returning reset acquire indication and propagates a reset breach indication to its adjacent bus. That reset acquire circulates and acquires the third bus and subsequent portals. For example, portal 1404 breaches 1408 to acquire bus 1446. The breach messages eventually circulate through all remote buses. The breach messages may reach leaf buses (a leaf bus has no other attached portals) or may close in on themselves when they pass through a bus bridge and discover that the adjacent portal has been acquired by the same candidate portal. The breach messages establish tentative busID assignments and routes; however, these are not activated until the final commit phase. During remote bus acquisition, the breach packets avoid previously acquired buses.

As in the primary bus acquisition, all bus acquisitions complete when the breach messages return to the initiating portal. After the breach is completed, the net knows the addresses that may be reclaimed, which addresses are free, and how many nodes are trying to claim free addresses.

The commit phase begins after the breach packets return bridge routing tables to the initiating prime portal 1402. During the commit phase, the bridge routing tables are updated and the busID assignments are finalized. The commit phase changes the bus bridge paths and opens closed bridges. During the commit phase, all portals receive assignments and routing information. After the commit phase is complete, all blocked portals are released and traffic may commence. Commit packets are sent, initiating the prime portal 1402 and traversing the interconnect topology 1400. The commit completes when the commit packets return to the prime portal 1402. Normal operation of the net is possible at this time, as the sending of the commit messages stops and the bridges become operational.

Figure 12A:
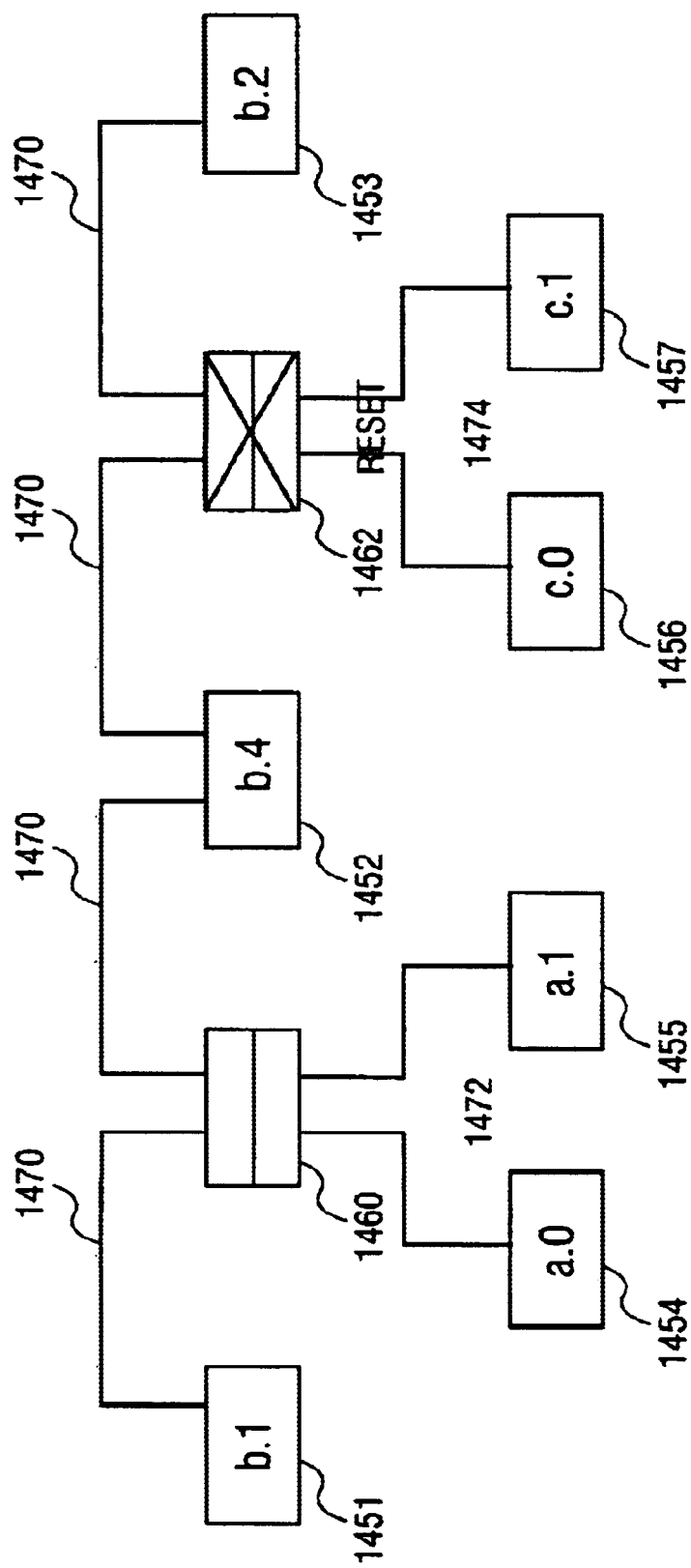
FIGS. 12A and 12B are block diagrams of one embodiment illustrating a bus reset on a bus.
Figure 12B:
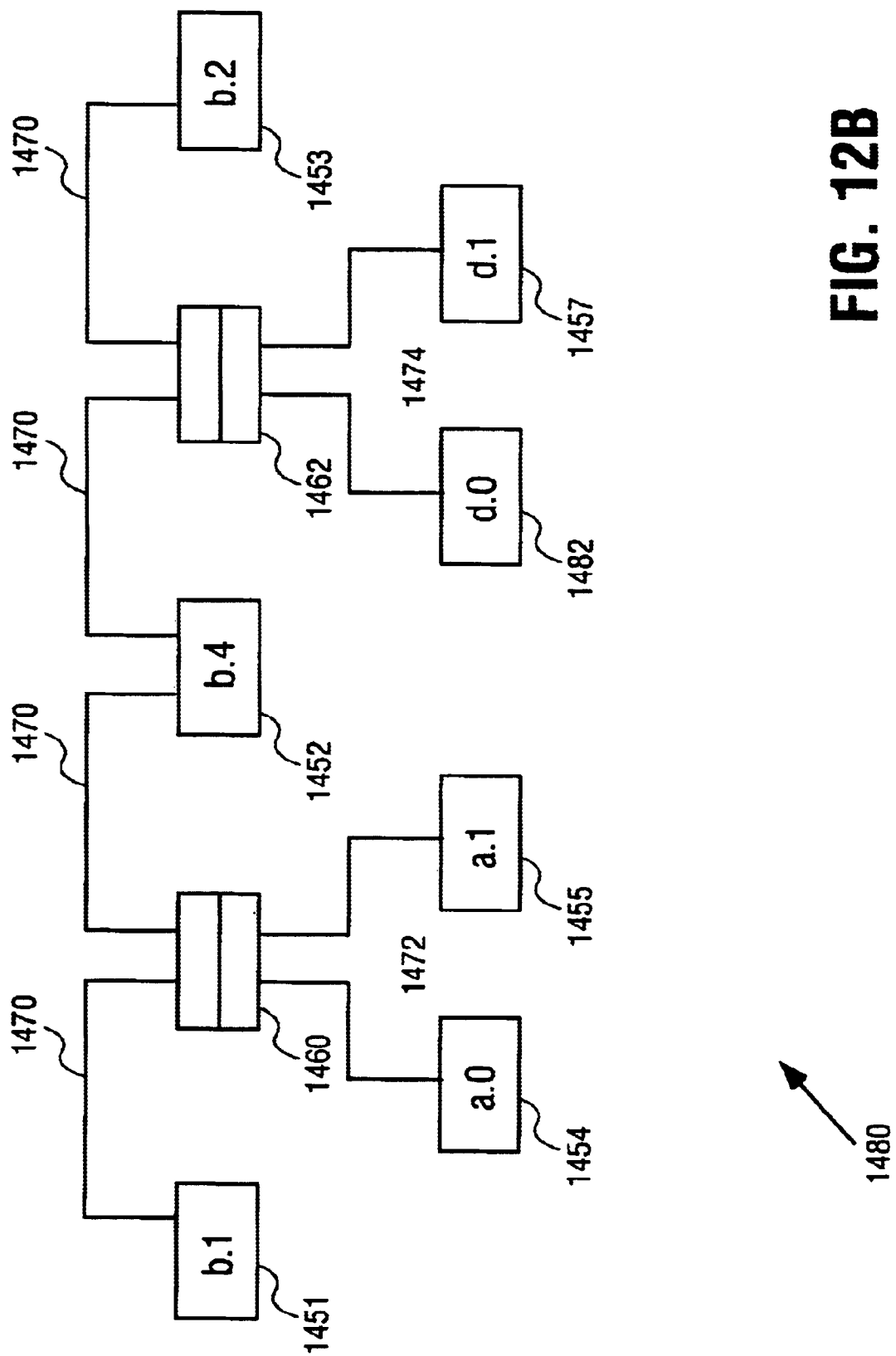

FIGS. 12A and 12B are block diagrams of one embodiment illustrating a bus reset on a bus. FIG. 12A is a block diagram of one embodiment of a bus bridge topology 1450 illustrating a bus reset on bus 1474. For example, the bus reset on bus 1474 may be a "configuring reset."

Referring to FIG. 12A, topology 1450 contains a number of nodes 1451, 1452, 1453, 1454, 1455, 1456, and 1457. Each node 1451–1457 is defined with a node identifier ("nodeID") for addressing purposes. In one embodiment, a nodeID is a 16-bit node identification address, which includes a 10-bit bus identifier ("busID") and a 6-bit physical identifier ("phyID") or a local identifier ("localID"). The busID identifies a bus within topology 1450 and the phyID identifies where the nodes are located on the bus. For the discussion that follows for node devices 1451–1457, busIDs are indicated by the letters a, b, and c, and the phyIDs are indicated by the numbers 0, 1, 2, and 4.

Topology 1450 also contains bus bridges 1460 and 1462, which interconnect bus 1470 with buses 1472 and 1474, respectively. Bus bridges 1460 and 1462 are also node devices, which operate as an interface and an intermediate agent between buses. In the example of FIG. 14a, bus bridge 1460 is a prime portal and bus bridge 1462 is an alpha portal. Bus 1470 refers to busID "b" and buses 1472 and 1474 refer to busIDs "a" and "c," respectively.

A bus reset is propagated on bus 1474 as a result of a configuration change. For example, a configuration change may occur on bus 1474 by replacing node 1456 with a different node, which may cause a bus reset. In one embodiment, a bus reset on bus 1474 stops all traffic on bus 1474 until the bus reset process is completed. A bus reset on bus 1474 occurs locally and causes devices on bus 1474 to be reconfigured. In one embodiment, bus bridge 1462 is responsible for assigning new busIDs to each device connected to bus 1474. In another embodiment, the alpha portal is responsible for assigning new busIDs.

In one embodiment, all devices on bus 1474 are assigned new busIDs regardless of the status of the device. For example, referring to bus topology 1480 in FIG. 12B, node 1482 replaced node 1456 in FIG. 12A and node 1457 remained unchanged. Nevertheless, both node 1482 and node 1457 receive new busIDs as indicated by the change of letter in the figure. For example, node 1456 is changed from "c.0" to "d.0" in node 1482 and node 1457 is changed from "c.1" to "d.1." In one embodiment, new busIDs are assigned that do not conflict with busIDs on other buses. For example, as shown in FIG. 12B, new busID "d" does not conflict with existing busIDs "a," "b," and "c."

In one embodiment, the routing tables in bus bridge 1462 are updated with the new busID assignments for nodes 1482 and 1484, and CSR registers in nodes 1482 and 1484 are updated informing nodes 1482 and 1484 of their busIDs. Furthermore, bus bridge 1462 may maintain an extended unique identifier (EUI) for each node connected on buses 1470 and 1474. In one embodiment, an EUI is a 64-bit code that is unique to each node. That is, no two nodes have the same EUI. In one embodiment, bus bridge 1462 is able to provide others with EUIs of nodes attached to the bus. The bus reset process also determines the phyID for each node on the bus. For example, the phyIDs for nodes 1482 and 1457 are obtained using next-neighbor ordering topology as illustrated in FIG. 7. The obtained phyIDs may also be updated in routing tables and CSR registers. In one embodiment, nodes connected with the bus performing a bus reset obtain the new busID and phyID for all the nodes on the bus using a net refresh message path as described in reference to FIG. 9.

Figure 13:
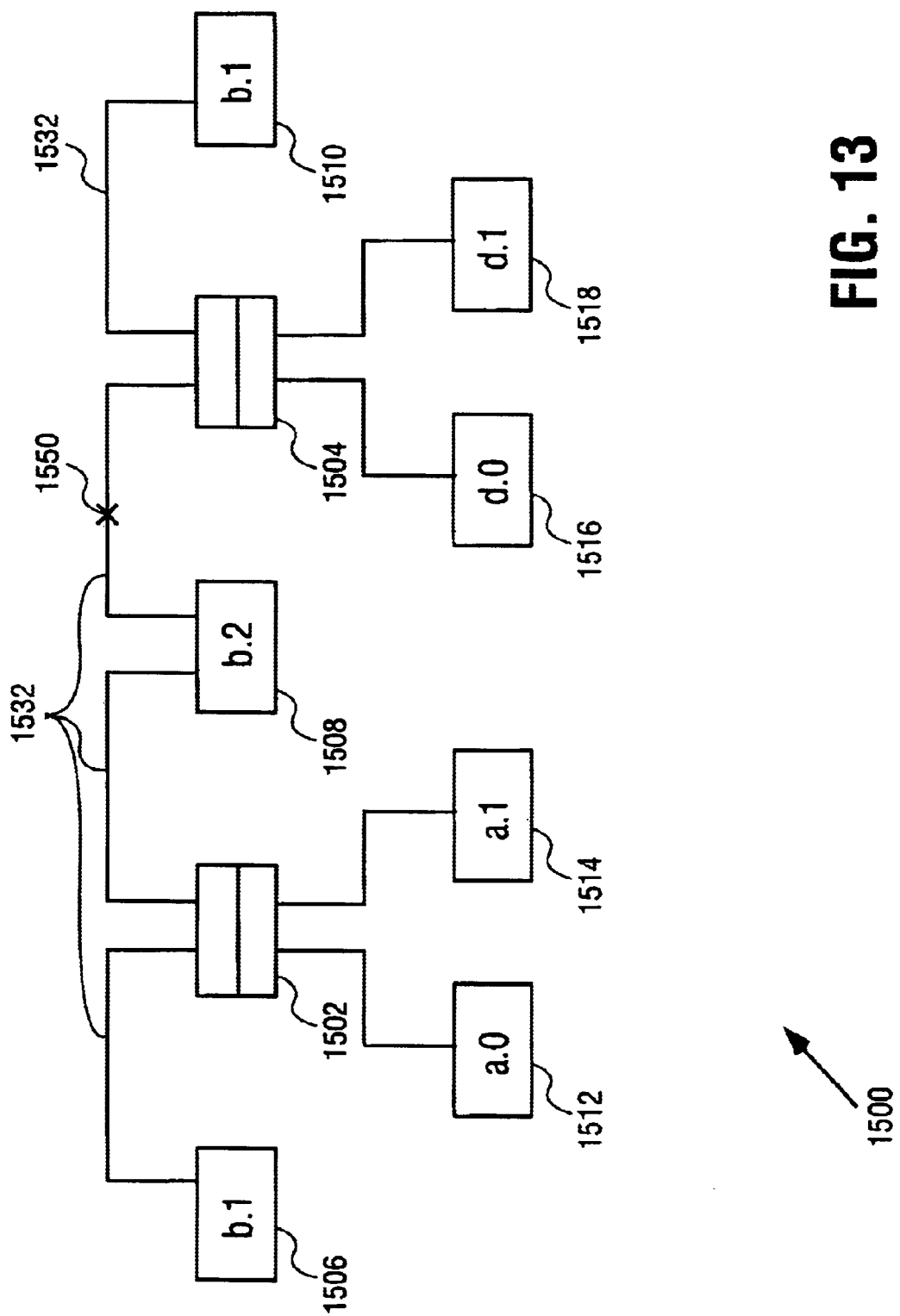
FIGS. 13, 14, and 15 are block diagrams of one embodiment for a secondary bus reset after node detachment.
Figure 14:
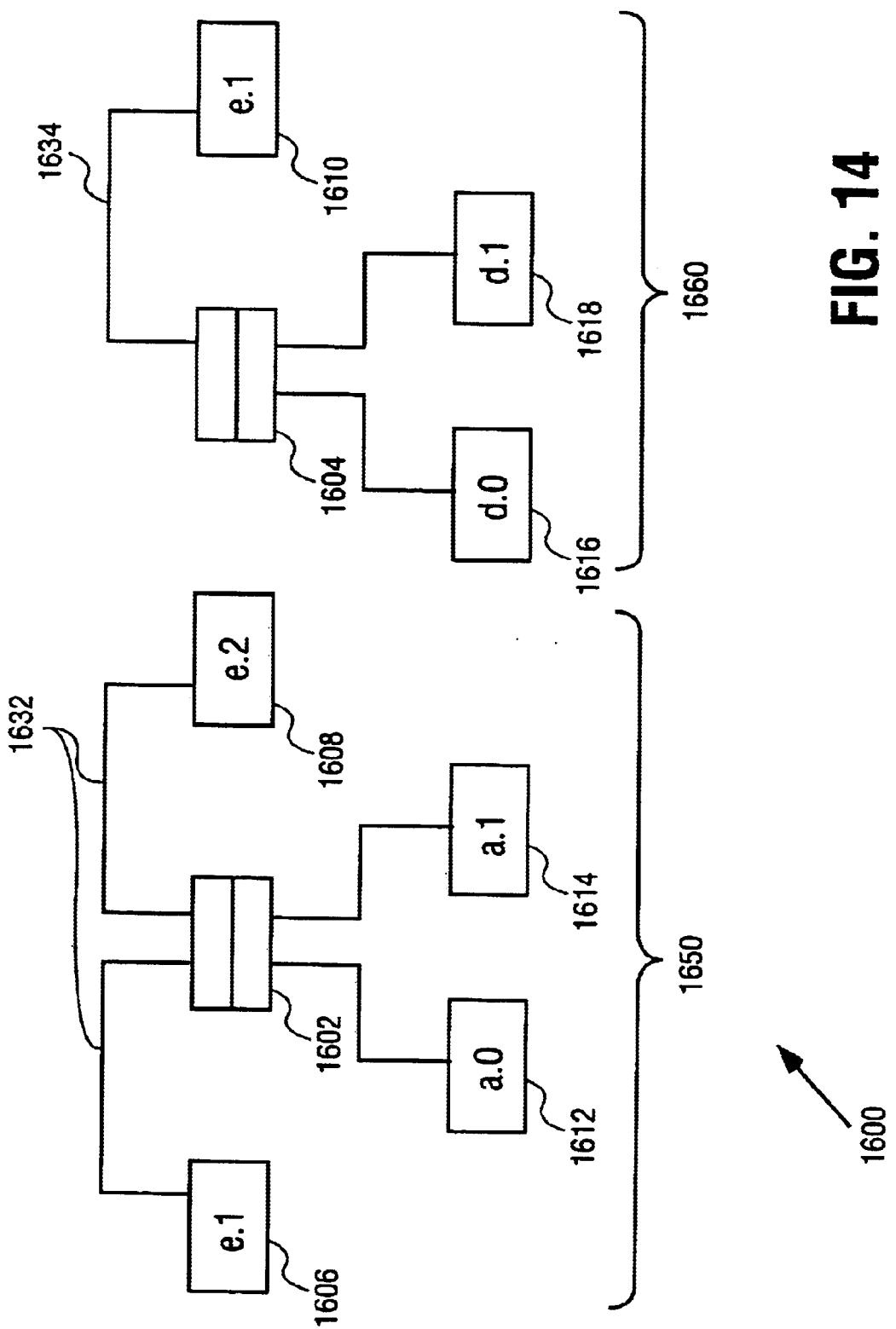
Figure 15:
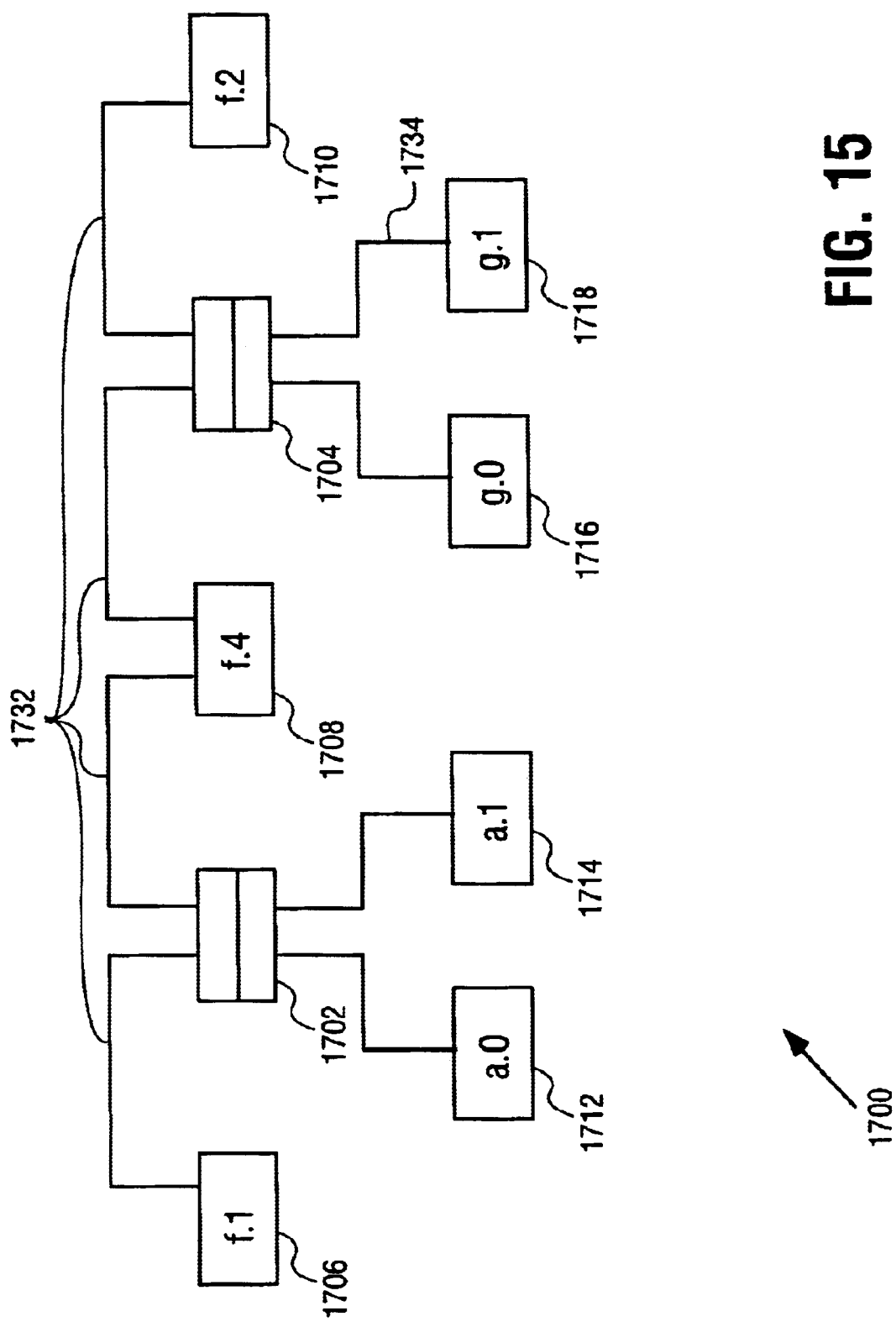

FIGS. 13, 14, and 15 are block diagrams of one embodiment for a secondary bus reset after node detachment.

FIG. 13 is a block diagram illustrating the subnet 1500 prior to this connection. Referring to FIG. 13, subnet 1500 consists of prime portal 1502 and secondary alpha portal 1504 and further includes nodes 1506, 1508, 1510, 1512, 1514, 1516, and 1518. Two subnets may be disconnected during operation of the interconnect by, for example, pulling a cable or detaching a bridge portal. During a disconnection, one subnet is referred to as the survivor subnet and one is referred to as the victim subnet. During a disconnection, both subnets at the dosconnection point receive new busIDs.

For example, if a disconnection occurs at point 1550 in FIG. 13, the two surviving subnets of subnet 1600 are as shown in FIG. 14. In FIG. 14, subnet 1650 includes portal 1602 and nodes 1606, 1608, 1612, and 1614. Subnet 1660 includes portal 1604 and nodes 1610, 1616, and 1618. The original bus 1532 is shown as buses 1632 and 1634. In this example, it is assumed that subnet 1650 is the survivor subnet and that subnet 1660 in the victim subnet. The nodes 1606 and 1608 on the survivor subnet 1650 receive new busID, as indicated by the change of letter in the figure. (For example, node 1506 is changed from "b.1" to "e.1" in node 1606.) In addition, node 1610 receives a new busID. The victim subnet 1660 identification is removed from the tables within the survivor 1650 portal tables. Thus, within survivor subnet 1650 previous busIDs or b, c, and d are invalidated and marked as previously used. Within the victim subnet 1660, the previously used busIDs are marked as invalid in preparation for a reconnect.

During the reconnection of the subnets, new busIDs are assigned within the victim subnet 1660. In addition, a new busID is assigned to the merged reset bus, as illustrated in FIG. 15. In FIG. 15, subnet 1770 includes nodes 1706, 1708, 1710, 1712, 1714, 1716, and 1718 and portals 1702, 1704. Thus, in the example of FIG. 15, new busID F is assigned to the merged bus 1732 and a new busID G is assigned to bus 1734 in the previous victim subnet 1660. Because busIDs B, C, and D were marked as invalid in the prior disconnection, these busIDs are no longer used. In addition, the assigned busID of E that was used in FIG. 14 to indicate the disconnection is also not used during the reconnection process. A new busID F is assigned to the merged, rejoined bus 1732. The survivor subnet 1650 has unchanged prime portal 1702 identifier (a in the example) and other survivor buses keep their assigned busID addresses. The victim subnet 1660 has a changed prime portal 1704 identifier and other victim buses are assigned new busID addresses, as required.

FIGS. 13, 14, and 15 illustrate one embodiment of a configuring net refresh. A configuring net refresh has the effect of assigning non-conflicting busID addresses to each of the attached buses. When busIDs conflict, either with the currently assigned busID or a dirty, (that is, previously assigned) busID, new free busIDs are assigned.

A cleansing net refresh is similar to a configuring net refresh as the recycling of "dirty" to "free" of stale busIDs by setting quarantines in each bus bridge portal. After the quarantines have been set, the portal may recycle dirty busIDs after a time delay of $T_{dirt}$. The $T_{dirt}$ value is the maximum time a transaction can remain queued before passing into a bus bridge. In one embodiment, a cleansing net refresh is performed when the number of dirty busIDs exceeds the number of free busIDs within the busID tables. The cleansing net refresh recycles the dirty busID stage to avoid the invocation of more disruptive purging net refresh. A cleansing net refresh is also invoked on a victim portion of the subnet to reduce the disruption of survivor subnet buses when the victim and survivor subnets are reconnected.

A purging refresh is performed when the number of desired busIDs exceeds the number of free busIDs. Although the cleansing refresh would eventually change busIDs from dirty to free, the purging refresh avoids the delay associated with the cleansing refresh recycling process. Because bus bridges may have previously queued (stale) transactions with dirty busID addresses, these queues are purged during a purging net refresh. This occurs quickly without timeout related delays. However, a purging net refresh disrupts currently active transactions.

When subnets are reattached, as exemplified in FIG. 15, it is necessary to consistently determine which nodes are survivor nodes and which are victim nodes when the two sets of bus addresses are collapsed into one. In one embodiment, the prime portal may be used to determine which portals are on the victim or survivor sub-net. The sub-net which contains the prime portal is the survivor subnet. The sub-net which acquires a new prime portal is called the victim sub-net. The prime portal is defined as the portal with the largest refreshID.

In one embodiment, the refreshID is determined by attaching a two bit preference to the EUI of the portals and using this value to determine the prime portal. The "EUI plus preference" value is transmitted with the net refresh messages from next neighbor to next neighbor and each portal votes on the refreshID value.

In one embodiment, the portal with the largest refreshID value is used as the prime portal. In an alternate embodiment, the portal with the smallest refreshID value may be used as the prime portal. In alternate embodiments, any manner of comparison or arithmetic ordering of EUI values may be used to determine a unique node such as the smallest bit-reversed EUI value.

In one embodiment, the EUI plus preference value is passed through the interconnect. This scheme has two purposes: 1) identify the prime portal to other portals; and (2) allow the prime portal to determine when all others have observed its messages, because only then do the messages return to the prime portal.

Figure 16:
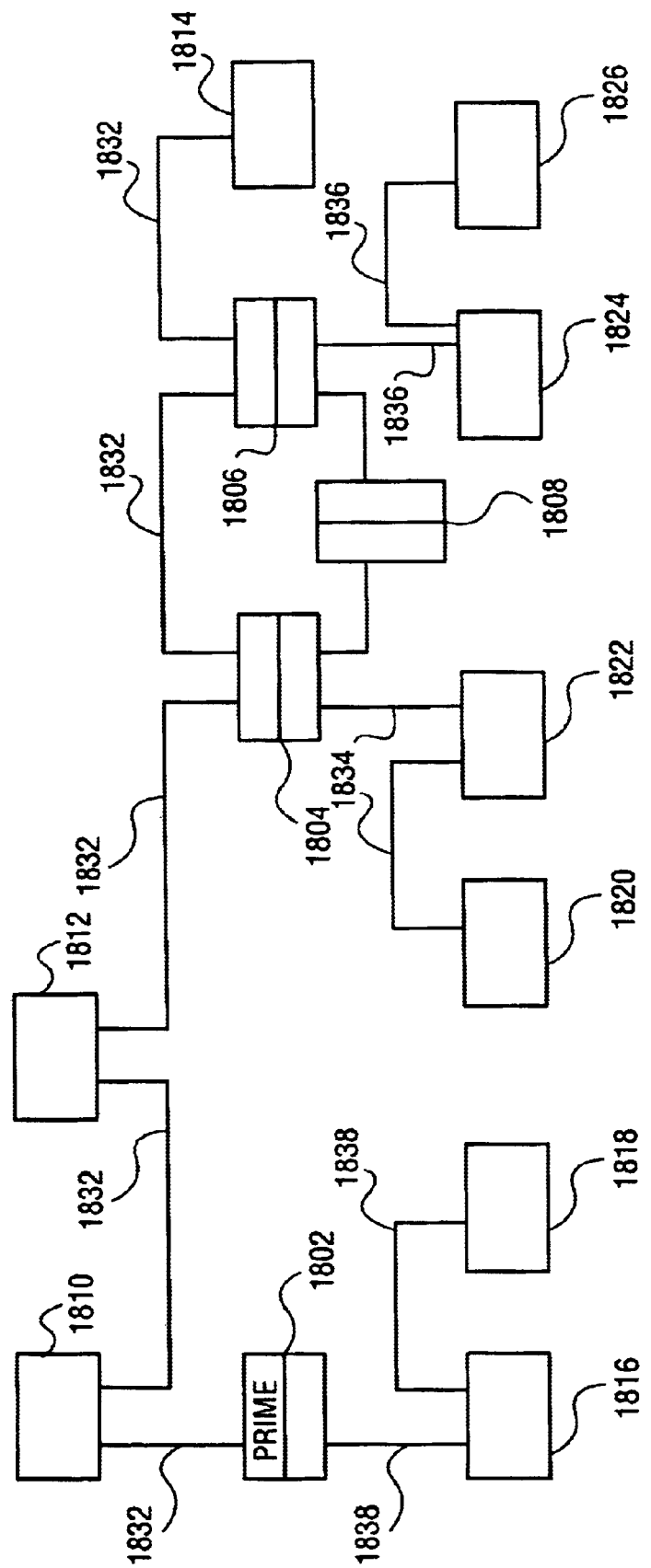
FIG. 16 is a block diagram of one embodiment for an interconnect broadcast topology.

FIG. 16 is a block diagram of one embodiment for an interconnect broadcast topology 1800. A broadcast message may be used after busIDs have changed, for example, when one or more nodes may have been removed, one or more nodes may have been added or the nodeIDs have changed within the interconnect. The broadcast is implemented as two-phase process: first, portals communicate between themselves using directed messages, as described herein, and, second, one of the portals, typically the alpha portal, uses a broadcast transaction to communicate the event to other bus-local nodes. Thus, only bus-local broadcast transactions are required to be sent. This is valuable because the IEEE 1394 standard serial bus defines mechanisms for bus local broadcast but has no provisions for flow controlling these writes based on remote bus loading. Under certain conditions, a bus bridge portal may receive more broadcasts than it can source on an adjacent bus, and some will be discarded. Thus, there is no assurance that normal broadcast transactions can be successfully forwarded through remote buses.

Referring to FIG. 16, any node (1810–1826) may initiate a broadcast message by writing that message to its bus local portal (1802–1808). The bus local portal (1802—1802) forwards this message to the next portal (next neighbor as described in reference to FIG. 7). The next neighbor then passes the message to its next neighbor. The message passing along buses 1832, 1834, 1836, and 1838 continues from one portal to the next until the message returns to its initial portal, where it is removed. Thus, if prime portal 1802 receives a broadcast from one of its nodes (1816, 1818), the broadcast message is passes to its next neighbor, portal 1804. Portal 1804 than the broadcasts the message to portal 1808, which broadcasts the message to portal 1806, which broadcasts the message to portal 1802. Once portal 1802 receives its own broadcast message, the message is removed and dropped.

Each broadcast message generates a broadcast write transaction when it enters a bus through the dominant portal, ensuring one and only one broadcast on each bus. The broadcast messages are implemented as a sequence of directed-write transactions, in which each transaction may be flow controlled. Thus, the broadcast messages are flow controlled and need not be discarded on congested bridges. In addition, the completion of a broadcast message is confirmed when it returns to the initiating portal, and broadcast messages may be used to establish routing paths within the interconnect.

Broadcast messages are designed to be idempotent, so that they may be safely retired once they are returned to the initiating portal. In order to accomplish this, bus bridge portals maintain a copy of the previously received message, discarding the second and following copies after accepting the first. The broadcast message writes are acknowledged, but no response is returned to the sending portal. Because there are no responses that must be distinctly labeled, this allows an identical transaction to be safely and immediately reused after a short acknowledge-missing delay.

To avoid circular dependency deadlocks, one portal in the circular list of portals receives the message in a logical request queue and outputs the message to the next portal on a second logical response queue. Deadlock is avoided by mandating that request queue messages never block the processing of response queue messages.

In one embodiment, a broadcast message may trigger the return of information from multiple nodes. This form of broadcast trigger/collection is referred to as "broadcall" in the backplane environment. Within the interconnect, a broadcall protocol that returns selected node addresses is referred to as address resolution protocol (ARP). In one embodiment, the information received from multiple nodes may be triggered by supplying the EUI of the portal or node as the broadcast message is passed along. Thus, information is appended to the broadcast message as it passes through each portal and finally returns to the initiating portal. As the information passes through each portal, the information may be maintained in tables within the portal for later use.

Figure 17:
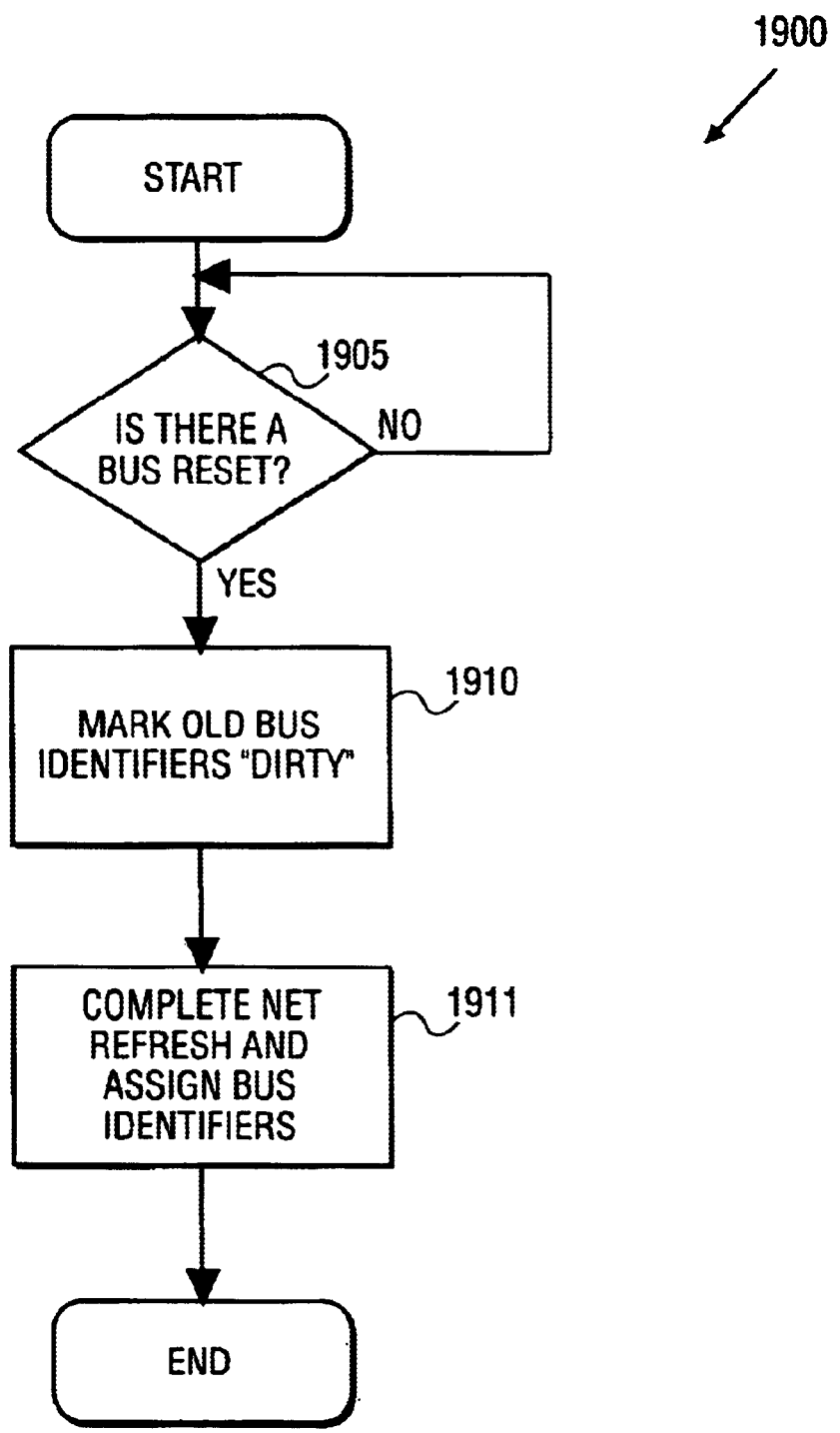
FIG. 17 is a flow diagram of one embodiment of a process for assigning new bus identifiers in an interconnect topology.

FIG. 17 is a flow diagram of one embodiment of a process 1900 for assigning new bus identifiers in an interconnect topology. In one embodiment, the interconnect topology comprises a number of nodes and a number of bus bridges.

Initially, the interconnect topology has been configured and is waiting for a topology change, which causes the interconnect topology to be reconfigured. Referring to FIG. 17, at processing block 1905, a topology change is determined by observing whether a bus reset has occurred. For example, a change in topology such as, for example, an addition or a removal of a node or subnet, causes a bus reset. Alternatively, a topology change can occur as a result of a net reset. In one embodiment, a bus reset is determined by a node initiating a "bus reset signal." If no bus reset is detected, process 900 returns to processing block 1905.

A node initiates a bus reset signal if it determines a topology change has occurred. For example, a node added to a bus will assert a bus reset signal to inform other nodes on the same bus that it has been added, and to begin the bus reset process. The bus reset process halts all traffic on the bus until the reset process is completed. In one embodiment, the bus reset signal is propagated to other nodes on the bus using the message path topology as described in reference to FIG. 9.

At processing block 1910, if a bus reset is determined, the bus reset process begins by a bus bridge marking old bus identifiers "dirty." The bus reset instigates a net refresh operation, and the net refresh operation assigns non-conflicting busIDs to all bridge portals. After assigning non-conflicting busIDs, at processing block 1911, a bus bridge may complete the bus reset process by assigning nodes on the bus a new busID regardless of the status or "state" of the node. Alternatively, a bus manager may assign new busIDs. In one embodiment, a bus manager may be determined using the next-neighbor ordering process as described in reference to FIG. 7, which is performed during a bus reset. For example, if three nodes having busIDs and phyIDs of a.0, a.1, and a.3 are originally connected with a bus, and a fourth node is added to the bus, the bus bridge or bus manager will assign all four nodes a new busID such as b.0, b.1, b.2, and b.3. In one embodiment, the bus bridge or bus manager will update routing tables and configure the CSR register of each node on the bus of its new busID. The node's phyID is assigned automatically during the bus reset process.

In one embodiment, the new busID will be non-conflicting such that it is different than other busIDs being used on other buses within the topology. In an alternate embodiment, the new busIDs are busIDs that have never been used in the topology. Alternatively, the new busIDs may be recycled busIDs, which have not been used after a predetermined amount of time. Process 1900 then ends after assigning busIDs.

Figure 18:
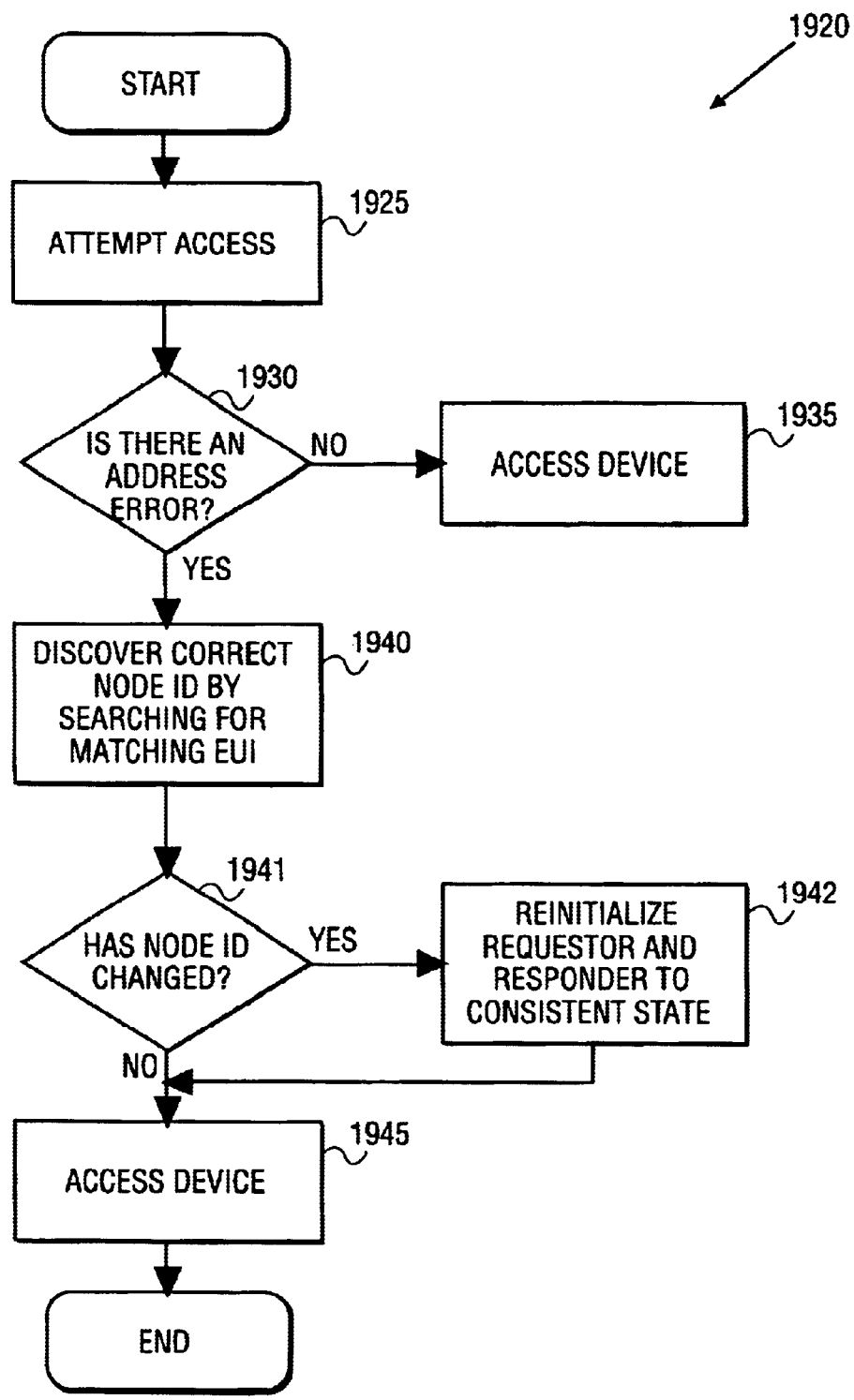
FIG. 18 is a flow diagram of one embodiment of a process for accessing nodes in an interconnect topology.

FIG. 18 is a flow diagram 1920 of one embodiment for accessing nodes in an interconnect topology. In one embodiment, the interconnect topology comprises a number of nodes and a number of bus bridges. The following process allows nodes to determine new busIDs without using conversion tables of new busID assignments being broadcast to each node in the topology. Initially, at processing block 1925, a first node attempts to access a second node on a different bus using a previous busID and phyID for the second node. For example, the first node may send a packet destined to the second node using the previous busID and phyID. In one embodiment, the packet is sent to a bus bridge, which forwards the packet to the second node.

At processing block 1930, the bus bridge determines if the correct address is being used for the packet, and determines if there is an address error. In one embodiment, if no topology changes have occurred, the previous busID and phyID will be valid as no reconfiguration of bus topology has occurred and the second node has not been assigned a new busID. Thus, if there is no address error, at processing block 1935, the bus bridge is able to forward the packet from the first node to the second node, and the first node is able to access the second node.

If there is an address error, at processing block 1940, the bus bridge sends the address error to the first node informing the first node that the address in the packet is invalid. In one embodiment, a bus reset has occurred on the bus connected with the second node, and the second node is assigned a new busID. For example, the second node may have had a previous busID and phyID of "f.0" and after a bus reset the second node is assigned a new busID and phyID of "g.0." As a result, the packet sent from the first node to the second node, using the previous address, will be an invalid address.

At processing block 1940, the first node determines the new nodeID for the second node having a new busID and phyID by using an extended unique identifier (EUI) of the second node. Each node in the interconnect topology is associated with a unique EUI. In one embodiment, an EUI is a 64 bit identifier in which the first 24 bits are used for identifying a manufacturer of a node, and the last 40 bits are used for identifying a specific node. Thus, each node has a unique identifier contained in its EUI. For example, the second node may have its last 40 bits of its EUI as "AA" that is used only by the second node. In one embodiment, the first node requests from the bus bridge portal the EUIs of nodes attached to its bus and continues doing this for each bus until the EUI of "AA," which corresponds to the second node, is found. As a result, the node at "g.0" is eventually found to have the EUI identifier of "AA."

At processing block 1941, the first node determines if the nodeID has changed for the second device. If the nodeID has changed for the second device, at processing block 1942, the first device or a requestor may be initialized in its status register that the nodeID for the second device or a responder has changed. Alternatively, the responder may also be initialized in its status register that its nodeID has changed. For one embodiment, the first device may be initialized to be aware of the the current state of the second device. Furthermore, the second device may be initialized to be aware of its current state.

Because the first node knows the new nodeID for the second node, the first node can access the second node. For example, the first node can send a packet having address of "g.0" such that the bus bridge can send the packet to the second node. As illustrated in the above process, there is no need to broadcast indications that busID assignments have changed to every node in the interconnect topology because this will be discovered when the node's old address is next accessed. Furthermore, nodes are not required to use conversion tables in accessing other nodes with new phyIDs because they have been assigned newbusIDs and therefore accesses to their old nodeID will be completed with error indications.

At processing block 1945, if the nodeID has not changed, the first device may access the second device using the current nodeID, and process 1920 ends.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method for using a new bus identifier in an interconnect, the interconnect having a plurality of nodes connected to multiple busses and at least one bus bridge, the method comprising:

determining a configuration change on any of the busses connected to the plurality of nodes, each node having a corresponding bus identifier; and assigning, by the at least one bus bridge, a new bus identifier for each node having a changed state if the node is currently connected to a bus affected by the configuration change is.

2. The method of claim 1, wherein at least one bus in the interconnect is substantially similar to the IEEE 1394 standard serial bus.

3. The method of claim 1, wherein assigning a new bus identifier assigns the new bus identifier such that the new bus identifier is non-conflicting with any other bus identifier being used in the interconnect.

4. The method of claim 1, wherein assigning a new bus identifier assigns the new bus identifier such that the new bus identifier has never been used in the interconnect.

5. The method of claim 1, wherein assigning a new bus identifier assigns the new bus identifier using a recycled bus identifier that has not been used in a predetermined amount of time.

6. The method of claim 1, wherein assigning a new bus identifier assigns the new bus identifier to a node regardless of the state of the node.

7. The method of claim 1, further comprising:
determining a local identifier for each node connected with the bus affected by the configuration change.

8. The method of claim 1, further comprising:
attempting an access of one of the nodes with the new bus identifier; and
determining the address of the one node using an extended unique identifier (EUI) that is unique to the one node if an address error occurs during the attempted access.

9. The method of claim 8, wherein determining the address includes:
sending a request for the address of the one node corresponding to the unique EUI for the one node.

10. The method of claim 1, wherein the configuration change is caused by a soft refresh, hard refresh, firm refresh, and net refresh.

11. The method of claim 1, wherein determining a configuration change determines an added node, removed node, subnet disconnection, or subnet reconnection.

12. An interconnect system, comprising:
a plurality of busses;
at least one bus bridge; and
a plurality of nodes connected to the plurality of busses, each node having a corresponding bus identifier and configured to be assigned a new bus identifier, wherein the at least one bus bridge is configured to assign the new bus identifier to each node having a change of state if the node is currently connected to a bus affected by a configuration change on any of the busses.

13. The interconnect system of claim 12, wherein at least one bus in the interconnect system is substantially similar to the IEEE 1394 standard serial bus.

14. The interconnect system of claim 12, wherein each node is assigned a new bus identifier such that the new bus identifier is non-conflicting with any other bus identifier being used in the interconnect system.

15. The interconnect system of claim 12, wherein each node is assigned a new bus identifier such that the new bus identifier has never been used in the interconnect system.

16. The interconnect system of claim 12, wherein each node is assigned a new bus identifier using a recycled bus identifier that has not been used in a predetermined amount of time.

17. The interconnect system of claim 12, wherein assigning a new bus identifier assigns the new bus identifier to a node regardless of the state of the node.

18. The interconnect system of claim 12, wherein each node is assigned a physical identifier.

19. The interconnect system of claim 12, wherein each node is configured to access a node with a new bus identifier and configured to determine the new bus identifier using an extended unique identifier (EUI) that is unique to the node with the new bus identifier if an error occurs in accessing the node with the new bus identifier.

20. The interconnect system of claim 19, wherein each node is configured to send a request for the address of the one of the plurality of nodes corresponding to the unique EUI.

21. The interconnect system of claim 12, wherein the configuration change is caused by a soft refresh, hard refresh, firm refresh, and net refresh.

22. The interconnect system of claim 12, wherein the configuration change is caused by an added node, removed node, subnet disconnection, or subnet reconnection.

23. An apparatus comprising:
means for connecting a device to a bus, said means for connecting the device to a bus being configured to be assigned a new bus identifier; and
means for interconnecting a plurality of busses, said means for interconnecting a plurality of busses being configured to assign the new bus identifier to each means for connecting having a change of state if the means for connecting is currently connected to a bus affected by a configuration change on any of the busses.

24. The apparatus of claim 23, wherein at least one of the plurality of busses is substantially similar to the IEEE 1394 standard serial bus.

25. The apparatus of claim 23, wherein the means for connecting is assigned a new bus identifier such that the new bus identifier is non-conflicting with any other bus identifier being used in the apparatus.

26. The apparatus of claim 23, wherein the means for connecting is assigned a new bus identifier such that the new bus identifier has never been used in the apparatus.

27. The apparatus of claim 23, wherein the means for connecting is assigned a new bus identifier using a recycled bus identifier that has not been used in a predetermined amount of time.

28. The apparatus of claim 23, wherein assigning a new bus identifier assigns the new bus identifier to the means for connecting regardless of the state of the means for connecting.

29. The apparatus of claim 23, wherein the means for connecting is assigned a physical identifier.

30. The apparatus of claim 23, wherein the means for connecting is configured to access a means for connecting with a new bus identifier and configured to determine the new bus identifier using an extended unique identifier (EUI) that is unique to the means for connecting with the new bus identifier if an error occurs in accessing the means for connecting with the new bus identifier.

31. The apparatus of claim 30, wherein the means for connecting is configured to send a request for the address of a means for connecting corresponding to the unique EUI.

32. The apparatus of claim 23, wherein the configuration change is caused by a soft refresh, hard refresh, firm refresh, and net refresh.

33. The apparatus of claim 23, wherein the configuration change is caused by an added means for connecting, removed means for connecting, subnet disconnection, or subnet reconnection.

* * * * *